United States Patent
Smit

(10) Patent No.: US 8,132,959 B2
(45) Date of Patent: Mar. 13, 2012

(54) MEDICAL CEMENT MONOMER AMPOULE CARTRIDGE FOR STORING THE AMPOULE, OPENING THE AMPOULE AND SELECTIVELY DISCHARGING THE MONOMER FROM THE AMPOULE INTO A MIXER

(75) Inventor: Karen L. Smit, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 593 days.

(21) Appl. No.: 12/201,464

(22) Filed: Aug. 29, 2008

(65) Prior Publication Data

US 2009/0057168 A1    Mar. 5, 2009

Related U.S. Application Data

(60) Provisional application No. 60/969,173, filed on Aug. 31, 2007.

(51) Int. Cl.
*B65D 25/08* (2006.01)
*B01F 13/06* (2006.01)

(52) U.S. Cl. ........ 366/182.3; 206/222; 222/87; 366/139

(58) Field of Classification Search .................. 366/139, 366/184, 189, 194–195, 308, 182.3; 206/219–222; 606/92; 222/80–91, 192, 236, 541.2
See application file for complete search history.

(56) References Cited

U.S. PATENT DOCUMENTS

| | | | |
|---|---|---|---|
| 1,744,893 A | 1/1930 | Hein | |
| 2,425,093 A | 5/1944 | Fosler | |
| 2,638,022 A | 2/1952 | Reyes | |
| 3,228,565 A | 1/1966 | Stanzel | |
| 3,366,369 A | 1/1968 | Ravisi | |
| 3,506,006 A | 4/1970 | Lange, Jr. | |
| 3,739,947 A | 6/1973 | Baumann et al. | |
| 3,742,988 A | 7/1973 | Kush | |
| 3,869,315 A | 3/1975 | Dolgner | |
| 3,892,237 A | 7/1975 | Steiner | |
| 3,986,838 A | 10/1976 | Reichert | |
| 4,043,335 A | 8/1977 | Ishikawa | |
| 4,178,928 A | 12/1979 | Tischlinger | |
| 4,185,582 A | 1/1980 | Bryant | |
| 4,218,525 A | 8/1980 | Selgin | |
| 4,227,528 A | 10/1980 | Wardlaw | |
| 4,241,850 A | 12/1980 | Speer et al. | |
| 4,246,229 A | 1/1981 | McBride et al. | |

(Continued)

FOREIGN PATENT DOCUMENTS

EP    1005900 A2 *   6/2000

(Continued)

OTHER PUBLICATIONS

USPTO ISA Search Report and Written Opinion for PCT App. No. PCT/US2007/021408, Aug. 2008.

*Primary Examiner* — Charles E Cooley

(57) ABSTRACT

A monomer handling unit for storing a ampoule of monomer and releasing the monomer from the ampoule when desired is provided. The monomer handling unit can be used to attach to an enclosed mixer and release a monomer component of the bone cement into the mixer to be mixed with a powder component of the bone cement. The monomer handling unit can also be used to release the liquid monomer into another mixer, such as one that is not enclosed.

20 Claims, 31 Drawing Sheets

U.S. PATENT DOCUMENTS

| | | | |
|---|---|---|---|
| 4,272,479 A | 6/1981 | Huneke et al. | |
| 4,298,777 A | 11/1981 | Bryant | |
| 4,306,554 A | 12/1981 | Schwartz et al. | |
| 4,312,344 A | 1/1982 | Nilson | |
| 4,328,754 A | 5/1982 | Goodman | |
| 4,340,007 A | 7/1982 | Hogan | |
| 4,375,504 A | 3/1983 | Jensen et al. | |
| 4,423,724 A | 1/1984 | Young | |
| 4,453,934 A | 6/1984 | Gahwiler et al. | |
| 4,483,049 A | 11/1984 | Gustavsson et al. | |
| 4,505,433 A | 3/1985 | Selenke | |
| 4,526,758 A | 7/1985 | Alengoz et al. | |
| 4,528,268 A * | 7/1985 | Andersen et al. | 435/31 |
| 4,533,641 A | 8/1985 | Holt | |
| 4,779,763 A * | 10/1988 | Klawitter | 222/80 |
| 4,952,065 A | 8/1990 | Kreuziger | |
| 4,968,302 A | 11/1990 | Schluter et al. | |
| 5,044,758 A | 9/1991 | Kurtz | |
| 5,181,909 A | 1/1993 | McFarlane | |
| 5,193,907 A * | 3/1993 | Faccioli et al. | 366/130 |
| 5,306,277 A | 4/1994 | Bryant et al. | |
| 5,393,497 A * | 2/1995 | Haber et al. | 422/554 |
| 5,435,645 A * | 7/1995 | Faccioli et al. | 366/130 |
| 5,545,460 A * | 8/1996 | Tanaka et al. | 428/137 |
| 5,571,282 A | 11/1996 | Earle | |
| 5,588,745 A * | 12/1996 | Tanaka et al. | 366/130 |
| 5,639,029 A | 6/1997 | Sundholm | |
| 5,709,668 A | 1/1998 | Wacks | |
| 5,934,803 A * | 8/1999 | Hutter | 366/139 |
| 5,975,751 A | 11/1999 | Earle | |
| 6,024,480 A * | 2/2000 | Seaton et al. | 366/130 |
| 6,042,262 A * | 3/2000 | Hajianpour | 366/139 |
| 6,145,703 A | 11/2000 | Opperman | |
| 6,176,607 B1 * | 1/2001 | Hajianpour | 366/139 |
| 6,296,149 B1 * | 10/2001 | Long | 222/82 |
| 6,312,149 B1 * | 11/2001 | Sjovall et al. | 366/130 |
| 6,439,427 B2 * | 8/2002 | Long | 222/1 |
| 6,516,977 B2 * | 2/2003 | Chan | 222/394 |
| 6,598,815 B2 | 7/2003 | Hsieh | |
| 6,626,328 B2 | 9/2003 | Ritsche et al. | |
| 6,676,664 B1 | 1/2004 | Al-Assir | |
| 6,743,203 B1 | 6/2004 | Pickhard | |
| 6,783,515 B1 | 8/2004 | Miller et al. | |
| 6,832,703 B1 * | 12/2004 | Scott et al. | 222/189.06 |
| 6,916,308 B2 | 7/2005 | Dixon et al. | |
| 7,048,743 B2 | 5/2006 | Miller et al. | |
| 7,073,936 B1 * | 7/2006 | Jonsson | 366/139 |
| 7,112,205 B2 | 9/2006 | Carrison | |
| 7,171,964 B2 | 2/2007 | Moore et al. | |
| 7,658,537 B2 * | 2/2010 | Coffeen et al. | 366/189 |
| 7,854,543 B2 * | 12/2010 | Coffeen et al. | 366/189 |
| 8,021,037 B2 * | 9/2011 | Krueger et al. | 366/189 |
| 2003/0155381 A1 * | 8/2003 | Chan | 222/394 |
| 2004/0193171 A1 | 9/2004 | DiMauro et al. | |
| 2004/0204715 A1 | 10/2004 | Evans et al. | |
| 2004/0215202 A1 | 10/2004 | Preissman | |
| 2004/0260304 A1 | 12/2004 | Faccioli et al. | |
| 2005/0070915 A1 | 3/2005 | Mazzuca et al. | |
| 2005/0105385 A1 | 5/2005 | McGill et al. | |
| 2005/0113762 A1 | 5/2005 | Kay et al. | |
| 2005/0113843 A1 | 5/2005 | Arramon | |
| 2005/0228396 A1 * | 10/2005 | Jonsson | 606/92 |
| 2005/0228397 A1 | 10/2005 | Malandain et al. | |
| 2006/0028907 A1 | 2/2006 | Barker et al. | |
| 2006/0052794 A1 | 3/2006 | McGill et al. | |
| 2006/0074433 A1 | 4/2006 | McGill et al. | |
| 2006/0101925 A1 | 5/2006 | Peng et al. | |
| 2006/0133193 A1 | 6/2006 | Arramon | |
| 2006/0164913 A1 * | 7/2006 | Arramon | 366/139 |
| 2006/0274601 A1 * | 12/2006 | Seaton | 366/139 |
| 2009/0057168 A1 * | 3/2009 | Smit | 206/221 |
| 2009/0171361 A1 * | 7/2009 | Melsheimer et al. | 606/93 |
| 2009/0257306 A1 * | 10/2009 | Coffeen et al. | 366/189 |
| 2010/0110820 A1 * | 5/2010 | Coffeen et al. | 366/43 |

FOREIGN PATENT DOCUMENTS

WO      2011/010956 A1 *   1/2011

* cited by examiner

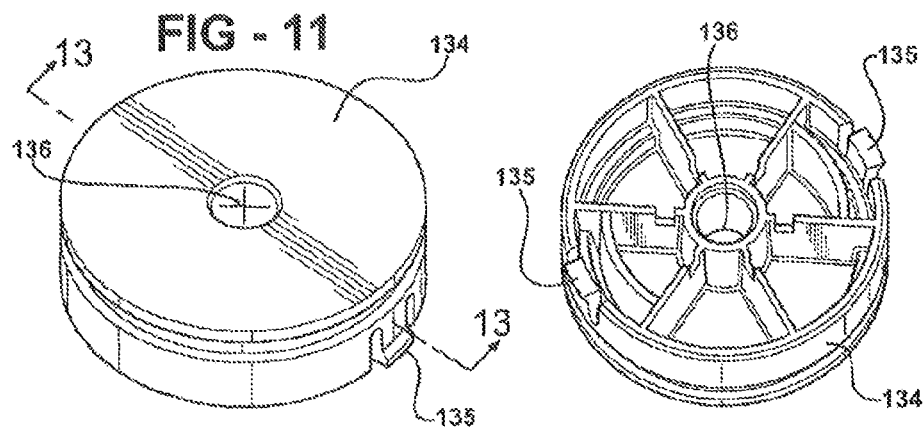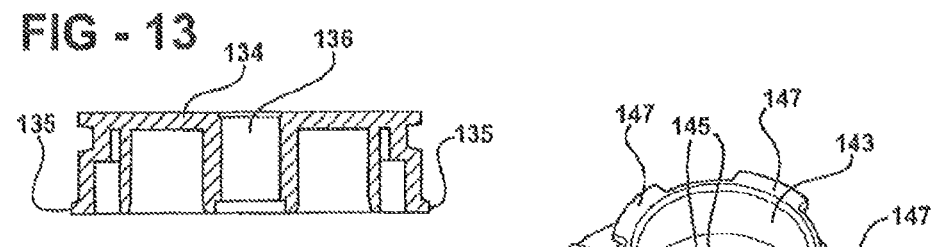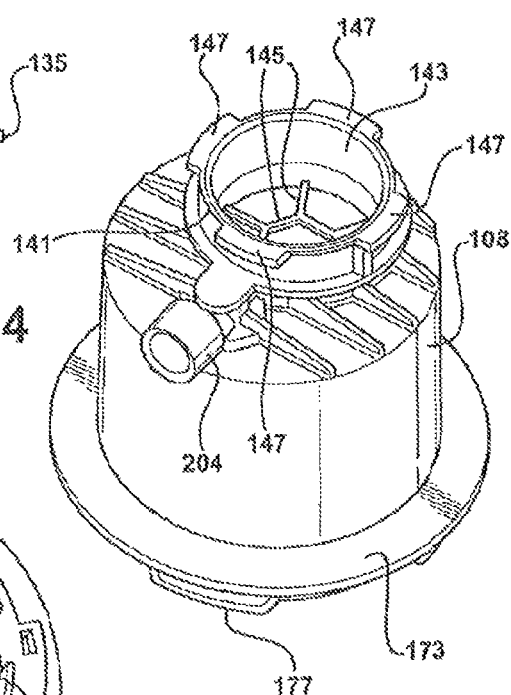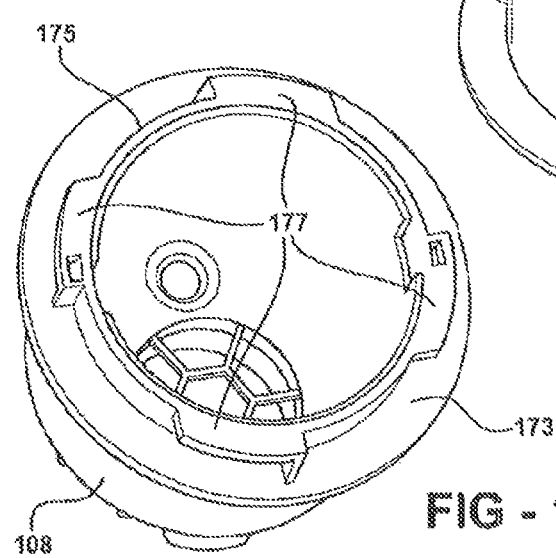

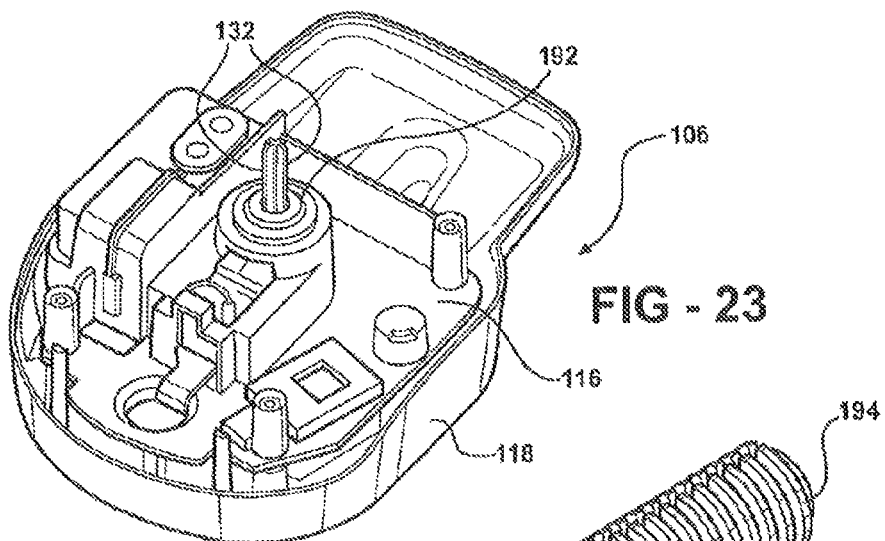
FIG - 23
FIG - 25
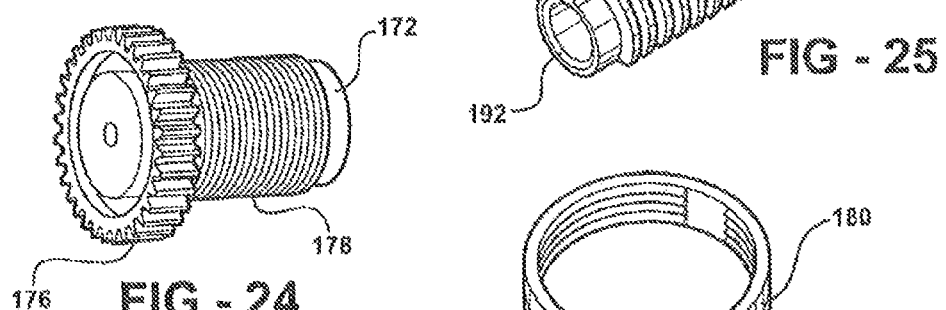
FIG - 24
FIG - 26
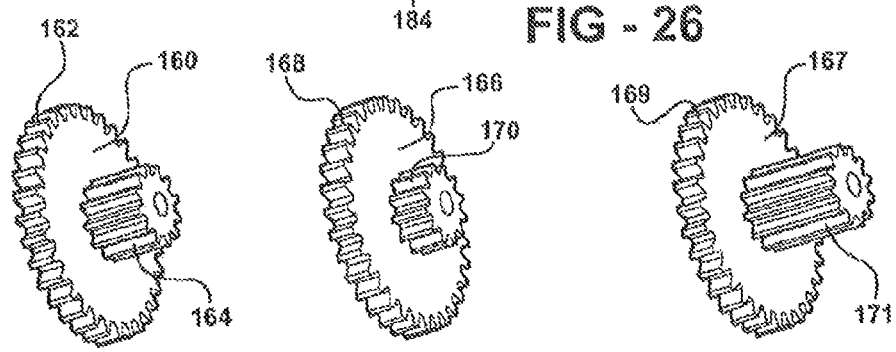
FIG - 27   FIG - 28   FIG - 29

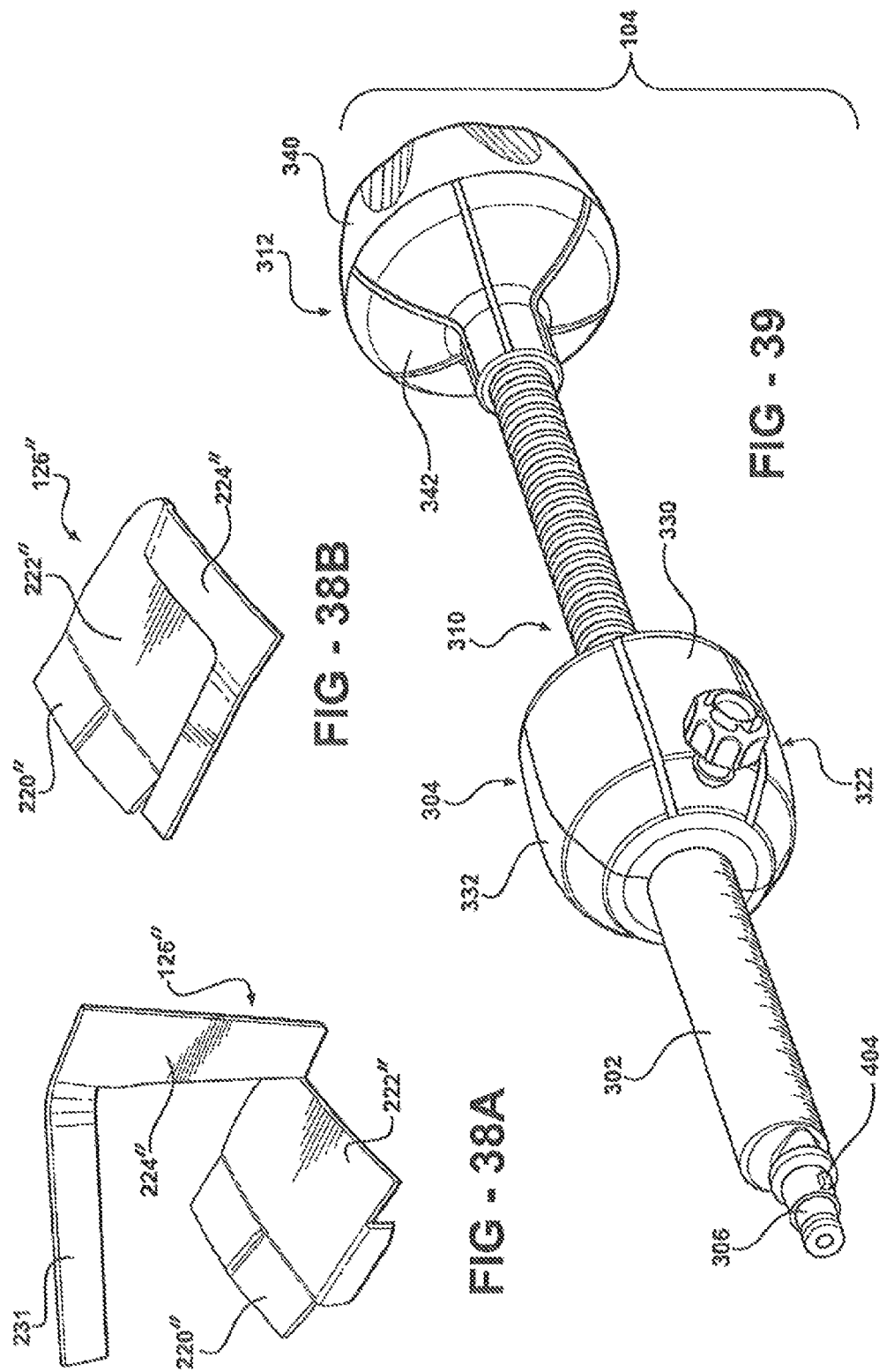

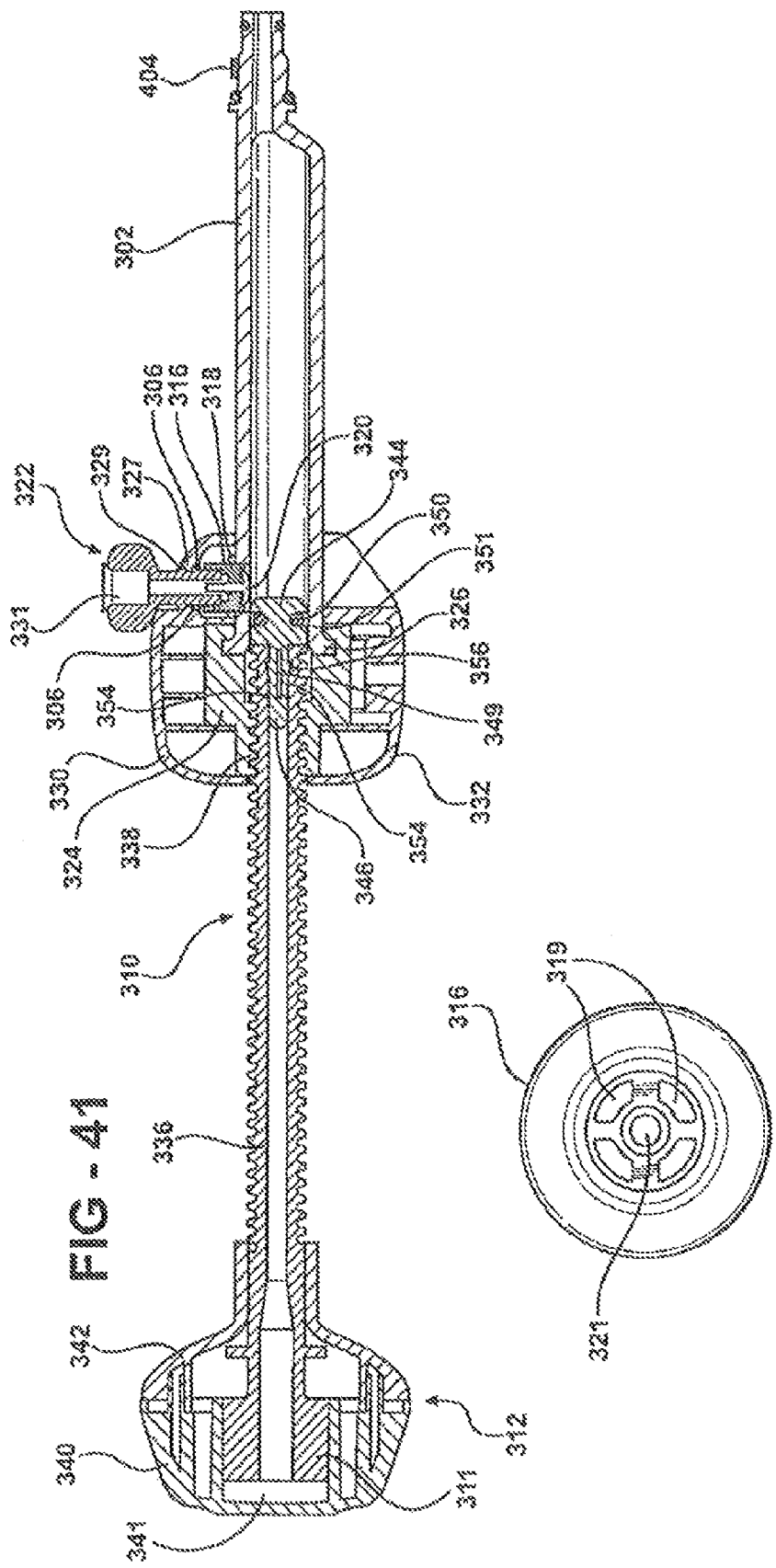

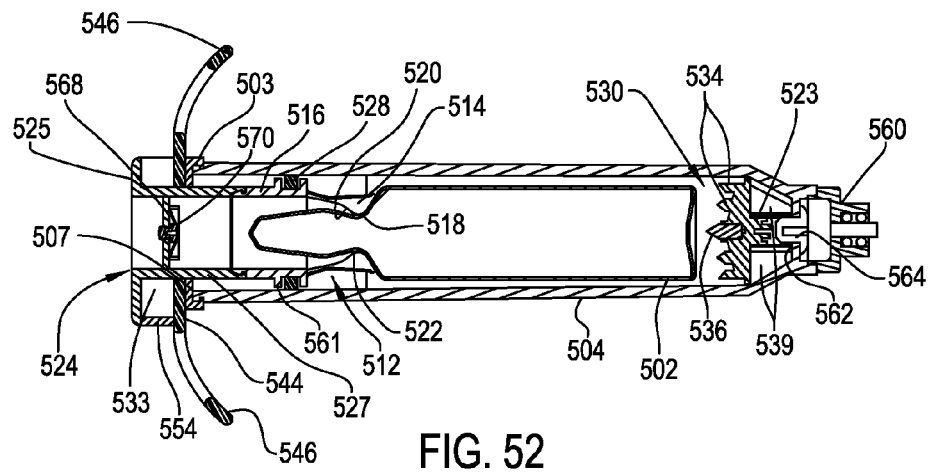
FIG. 52
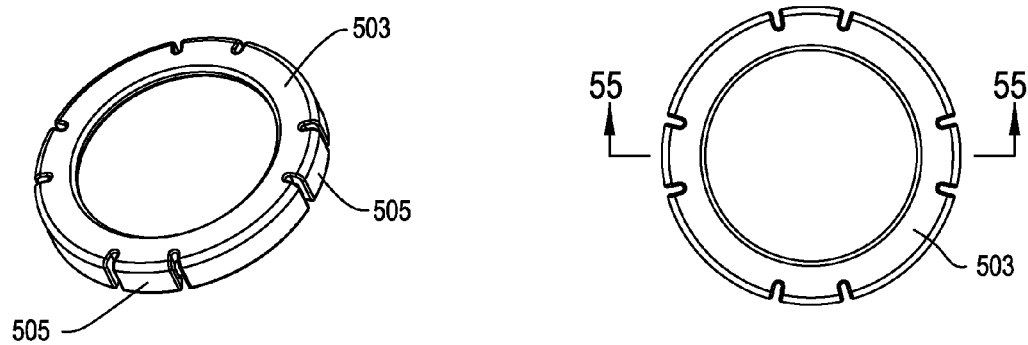
FIG. 53
FIG. 54
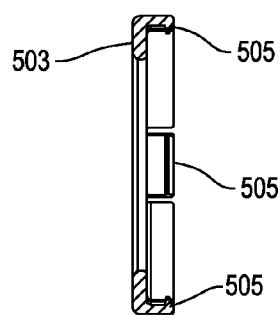
FIG. 55

MEDICAL CEMENT MONOMER AMPOULE CARTRIDGE FOR STORING THE AMPOULE, OPENING THE AMPOULE AND SELECTIVELY DISCHARGING THE MONOMER FROM THE AMPOULE INTO A MIXER

CROSS-REFERENCE TO RELATED APPLICATIONS

This application claims the benefit of and priority to U.S. provisional application Ser. No. 60/969,173, filed on 31 Aug. 2007 and incorporated herein in its entirety.

FIELD OF THE INVENTION

The present invention is related to a unit for storing an ampoule of bone cement monomer and releasing the monomer from an ampoule when desired. The unit can be attached to a bone cement mixer.

BACKGROUND OF THE INVENTION

Bone cement is used to, as the name implies, hold bone sections together. In some medical procedures, bone cement is also used to hold other devices, such as implants to bone. Bone cements consist of two primary components: a solid component, polymethyl methacrylate (PMM or PMMA), and a liquid monomer, methylmethacrylate (MMA). The solid component is typically a white powder consisting of copolymers based on the PMMs. These two components are mixed to form a polymethyl methacrylate bone cement. Liquid monomers are highly volatile. At a minimum, in the vapor state, monomers are displeasing to the nose. Monomer vapors can also irritate the skin, eyes, and respiratory tract.

Bone cement mixing and delivery systems are well known for mixing the separate components of bone cement together to form a uniform bone cement mixture and then delivering that mixture to a target site. Typically, such systems employ a mixer having a handle for manually mixing the components. Once mixed, the mixture is then manually transferred to a delivery device such as a syringe. The syringe is used to inject the mixture into the target site. Examples of target sites include medullary canals for total hip arthroplasty procedures, vertebral bodies for vertebroplasty or kyphoplasty procedures, and other sites in which bone cement is required.

Often, the types of bone cements used in these procedures have short working windows of only a few minutes thereby affecting the amount of time available for mixing and delivering the mixture to the target site. Current systems require a great deal of user interaction in set-up, including manually mixing the bone cement components and manually transferring the mixture to the delivery device. This user interaction delays delivery of the mixture to the target site, while also wasting the user's energy, which is preferably conserved to focus on the medical/surgical procedure itself. As a result, there is a need for bone cement mixing and delivery systems that are capable of quick set-up, with little user interaction.

One example of a bone cement mixing and delivery system that attempts to improve set-up time is shown in U.S. Pat. No. 5,571,282 to Earle. Earle discloses a motorized mixer that is used to mix the bone cement components. The mixer mixes the bone cement components a pre-selected amount of time, as set by the user. At the end of the pre-selected time, the mixer stops automatically and pressure is applied to the mixture to push the mixture out through a port in the bottom of the mixer to a syringe or delivery cartridge.

The release of odors and gases associated with the bone cement components can also be undesirable. As a result, there is also a need for bone cement mixing and delivery systems that are substantially self-contained such that the odors and gases associated with the bone cement components are not substantially released during mixing or transfer.

One example of a bone cement mixing and delivery system that provides such containment is shown in U.S. Pat. No. 5,193,907 to Faccioli et al. Faccioli et al. discloses an apparatus for mixing and delivering bone cement formed from liquid and powder components. The apparatus comprises a cylindrical body and a plunger slidable within the body. A powder chamber for storing the powder component is defined between the plunger and a distal end of the body. A glass ampoule storing the liquid component is disposed inside the plunger. To mix the components, a user presses a plug in the plunger's proximal end downwardly to urge a tip of the glass ampoule against a cammed surface (or against a shattering assembly) to release the liquid component. The liquid component then passes through a filter mounted to a head of the plunger and out channels defined through the head to enter the powder chamber. The liquid and powder components are mixed by shaking the body to form the bone cement mixture. After mixing, the plunger is used to press the bone cement mixture out of a distal aperture in the body and through a flexible conduit to a target site.

Other ways in which the prior art attempts to contain the odors and gases associated with the bone cement components is to contain the liquid component, usually the most noxious, within a self-contained handling unit that provides a barrier between the user and a monomer of the liquid component. An example of this type of unit is shown in U.S. Pat. No. 7,073,936 to Jonsson. Jonsson discloses an inner container enclosing a glass ampoule containing a liquid monomer of bone cement and a device for breaking the glass ampoule so that its contents can be sucked into a mixing vessel under partial vacuum. The device for opening the ampoule includes a threadable cap for pushing downward on the ampoule.

The prior art also attempts to prevent release of the monomer and its vapors by using a cover. One device uses a needle protector positioned over a needle. Another assembly uses a sealing plug positioned over a needle. In both cases, the cover prevents the release of the monomer and its vapors prior to removal of the cover. However, once removed, the monomer and its vapors can still be inadvertently dripped or otherwise released prior to use.

The prior art also relies on either breaking or piercing the ampoule to release the monomer contained within the ampoule. Some assemblies rely on pushing the ampoule against an inclined surface to break the ampoule along a weak point. Other assemblies rely on pushing a single cutting point or needle against the ampoule to pierce the ampoule. This can result in less than the entire contents of the ampoule being released and mixing with the powder.

SUMMARY OF THE INVENTION

The present invention provides a bone cement mixing and delivery system. The system comprises a mixer for mixing separate components of bone cement to form a uniform bone cement mixture. The system also comprises a delivery device for receiving the mixture from the mixer and delivering the mixture to a target site. A transfer mechanism facilitates automatic transfer of the mixture from the mixer to the delivery device. In one aspect of the invention, mixing and transfer occurs while the mixture remains contained within the system. In other words, a user's exposure to the bone cement mixture is minimized.

In one aspect of the invention, the delivery device is connected to the mixer by a transfer conduit and the mixture is automatically pumped from the mixer to the delivery device through the transfer conduit upon completion of mixing.

In another aspect of the invention, the delivery device is automatically primed when the mixture is transferred from the mixer to the delivery device.

In yet another aspect of the invention, an enlarged luer-lock connector is used to make a luer-lock connection between the delivery device and a delivery cannula used to convey the mixture from the delivery device into the target site. The target site is a vertebral body that is penetrated by the delivery cannula and then injected with the mixture to perform a vertebroplasty procedure.

The present invention also provides a monomer handling unit for storing an ampoule of monomer and releasing the monomer from the ampoule when desired.

In one aspect of the invention, the monomer handling unit is attached to the mixer of the bone cement mixing and delivery system to release a monomer component of the bone cement into the mixer to be mixed with a powder component to form the mixture.

In another aspect of the invention, the monomer handling unit comprises a cartridge and a plunger slidably disposed in the cartridge. A ampoule storing a monomer is secured to the plunger. A push cap is fixed to the plunger to slide the plunger and ampoule distally in the cartridge by pressing the push cap. A shattering assembly is disposed inside the cartridge to shatter the bottom of the ampoule upon sliding the plunger and ampoule distally in the cartridge. A handle locks to the push cap once the push cap and plunger have been moved a predetermined distance in the cartridge and the ampoule has been broken to release the monomer. At this point the handle is then pulled proximally, thereby pulling the push cap and plunger, while allowing air inside the cartridge, and then the push cap is depressed distally to urge the monomer out of the cartridge.

In still another aspect of the invention, the monomer handling unit comprises a cartridge and a plunger slidably disposed in the cartridge. A ampoule storing a monomer is secured to the plunger. A push cap is fixed to the plunger to slide the plunger and ampoule distally in the cartridge by pressing the push cap. A shattering assembly is disposed inside the cartridge to shatter the bottom of the ampoule upon sliding the plunger and ampoule distally in the cartridge. At this point the push cap is then pulled proximally, thereby pulling the push cap and plunger, while allowing air inside the cartridge, and then the push cap is depressed distally to urge the monomer out of the cartridge. In this aspect of the invention, a separate handle is not locked to the push cap.

BRIEF DESCRIPTION OF THE DRAWINGS

These and other objects, features and advantages of this invention will be apparent from the following detailed description of the preferred embodiment and accompanying drawings in which:

FIG. 11 is a top perspective view of a piston of the mixer;
FIG. 12 is a bottom perspective view of the piston;
FIG. 13 is a cross-sectional view of the piston taken generally along the line 13-13 in FIG. 11;
FIG. 14 is a top perspective view of a mixer housing of the mixer;
FIG. 15 is a bottom perspective view of the mixer housing;
FIG. 23 is a top perspective view of the base of the mixer;
FIG. 24 is a perspective view of a transfer gear;
FIG. 25 is a perspective view of a driver;
FIG. 26 is a perspective view of a switch nut;
FIGS. 27-29 are perspective views of various spur gears;
FIGS. 35A-38B are top perspective views of alternative mixing paddles in normal and flattened states;
FIG. 39 is a top perspective view of the delivery device;
FIG. 41 is a cross-sectional view of the delivery device;
FIG. 42 is a top view of a valve housing of the delivery device;
FIG. 47 is a cross-sectional view of the extension tube and the enlarged luer-lock connector;
FIG. 48 is a perspective view of a lock fitting of the extension tube;

FIG. 52 is a cross-sectional view of the monomer handling unit taken generally along the line 52-52 in FIG. 50 illustrating a glass ampoule stored in the monomer handling unit;

FIG. 53 is a top perspective view of a lid of the monomer handling unit;

FIG. 54 is a top view of the lid;

FIG. 55 is a cross-sectional view of the lid taken generally along the line 55-55 in FIG. 54;

DETAILED DESCRIPTION OF THE INVENTION

For the purpose of promoting an understanding of the present invention, references are made in the text hereof to exemplary embodiments of a medical cement monomer ampoule cartridge, only some of which are depicted in the figures. It should nevertheless be understood that no limitations on the scope of the invention are thereby intended. One of ordinary skill in the art will readily appreciate that modifications such as those involving the materials from which the components are made, the size of the components, functional equivalents of the elements, and the inclusion of additional elements do not depart from the spirit and scope of the present invention. Some of these possible modifications are discussed in the following description. Therefore, specific details disclosed herein are not to be interpreted as limiting, but rather as support for the claims and as a representative basis for teaching one skilled in the art to employ the present invention in virtually any appropriately detailed system, structure, or manner.

As used herein, "distal" refers to the end of the monomer handling unit from which the cement monomer is discharged, and "proximal" refers to the end of the monomer handling unit away from the end of the monomer handling unit from which the cement monomer is discharged. The terms "substantially" and "approximately," as used herein, may be applied to modify any quantitative representation that could permissibly vary without resulting in a change in the basic function to which it is related.

Figure 1:
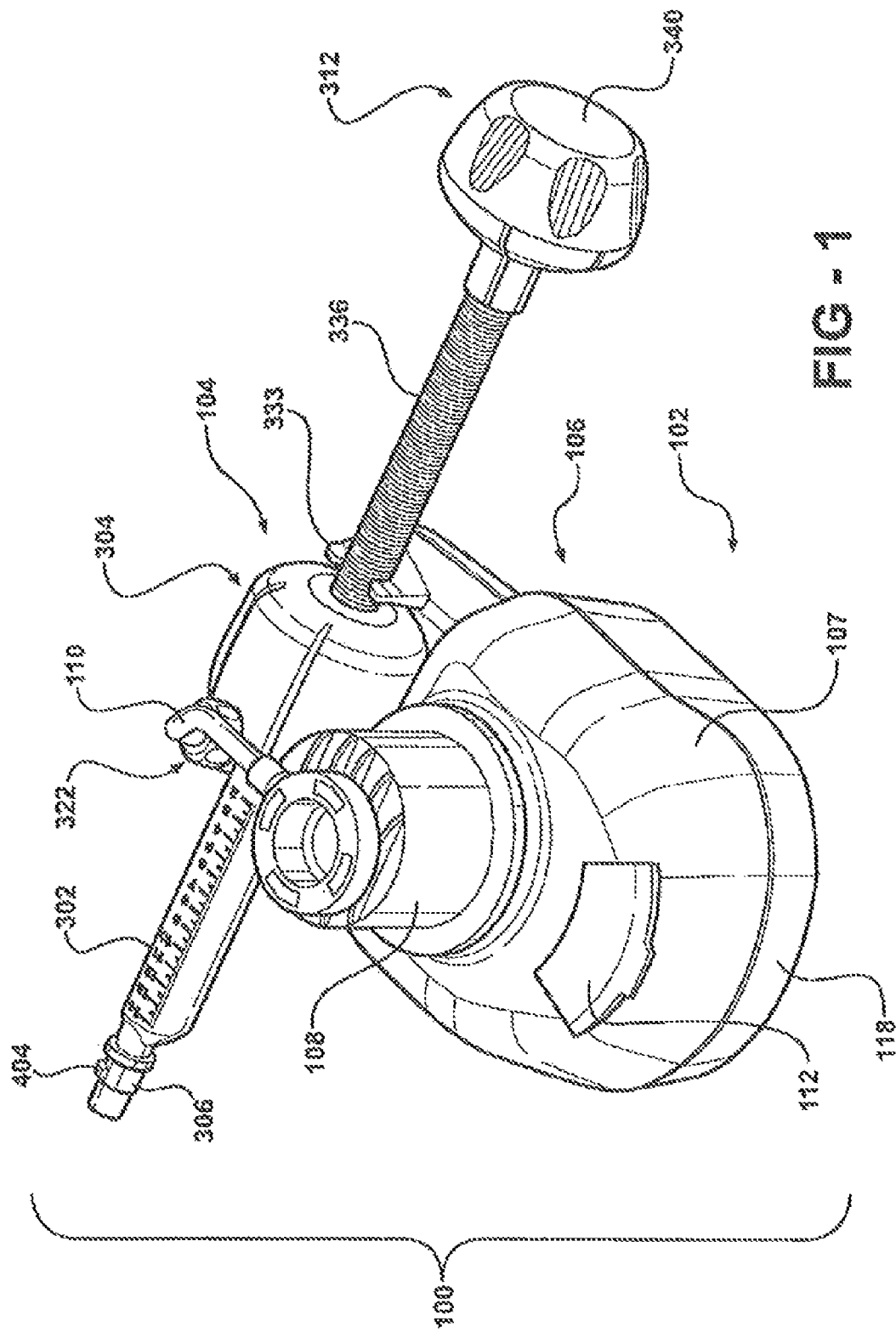
FIG. 1 is a top perspective view of a bone cement mixing and delivery system including a mixer and a delivery device.

Referring in more detail to the drawings, a bone cement mixing and delivery system of the present invention is generally shown at 100 in FIG. 1. The bone cement mixing and delivery system 100 preferably includes a mixer 102 to mix separate components of bone cement to form a bone cement mixture and a delivery device 104 to deliver the mixture to a target site. The target site may be an anatomical site such as a vertebral body or the target site may be in or near an implant.

The system 100 is useful in any procedure in which bone cement or any other mixture is required, particularly when time is a constraint and exposure of the material or its vapors is to be minimized. The system 100 is capable of mixing the bone cement components and automatically transferring the mixture to the delivery device 104 upon completion of mixing with little or no operator interaction. This reduces variability in mixing between users and creates consistency across multiple users. This automatic transfer feature reduces time and energy otherwise spent by a user to manually mix and transfer the mixture to a delivery device such as a conventional syringe. The system 100 also reduces exposure of the user to the bone cement components during mixing and transfer when compared to conventional mixing and delivery devices.

I. Mixer

Figure 2:
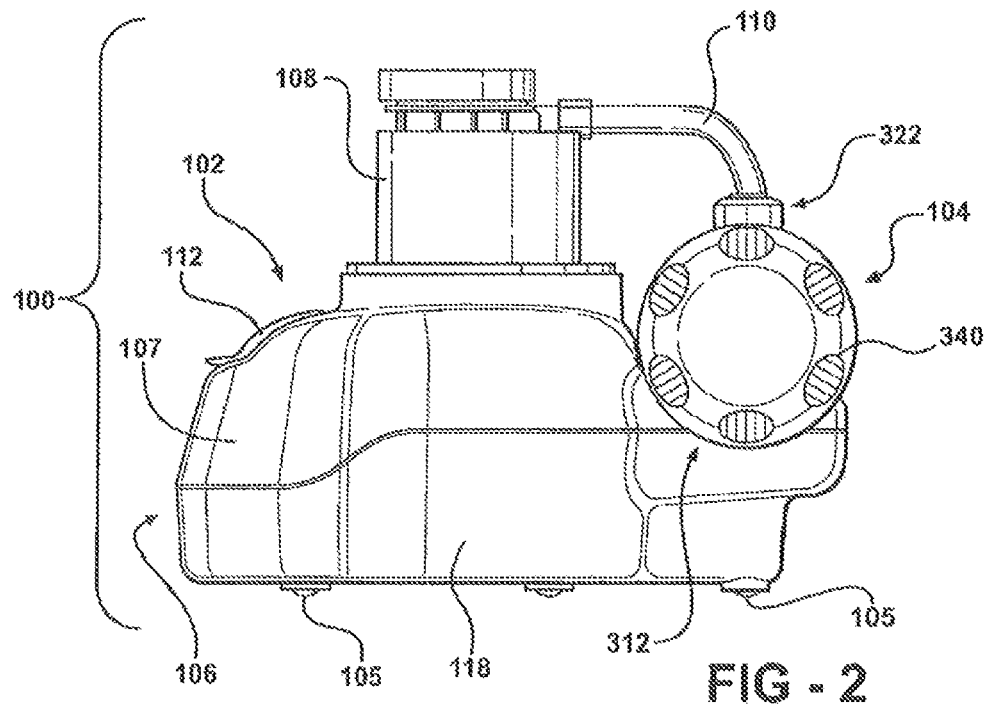
FIG. 2 is a side elevational view of the system of FIG. 1.
Figure 3:
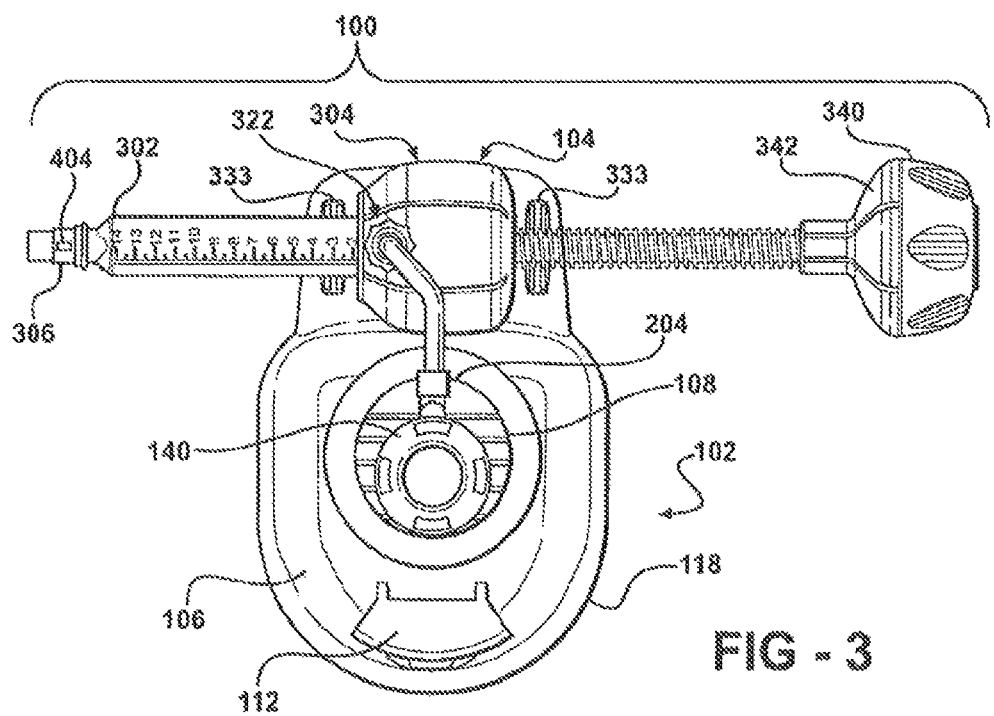
FIG. 3 is a top view of the system of FIG. 1.

Referring to FIGS. 1-3, the mixer 102 includes a base 106 for supporting the mixer 102 on a surface. The base 106 includes rubber feet 105 for gripping the surface. A casing 107 mounts to the base 106 to cover the base and provide an aesthetically pleasing shape to the mixer 102. A mixer housing 108 is coupled to the casing 107. A transfer conduit 110 links the mixer housing 108 to the delivery device 104. The transfer conduit 110 transfers the mixture from the mixer 102 to the delivery device 104. A switch cover 112 is pivotally mounted to the casing 107 to protect a switch button 114 (see FIG. 4) used to begin operation of the mixer 102. Once the switch button 114 is pressed, the bone cement components are mixed together to form the mixture and then, once mixing is complete, the mixture is automatically transferred through the transfer conduit 110 to the delivery device 104.

Figure 4:
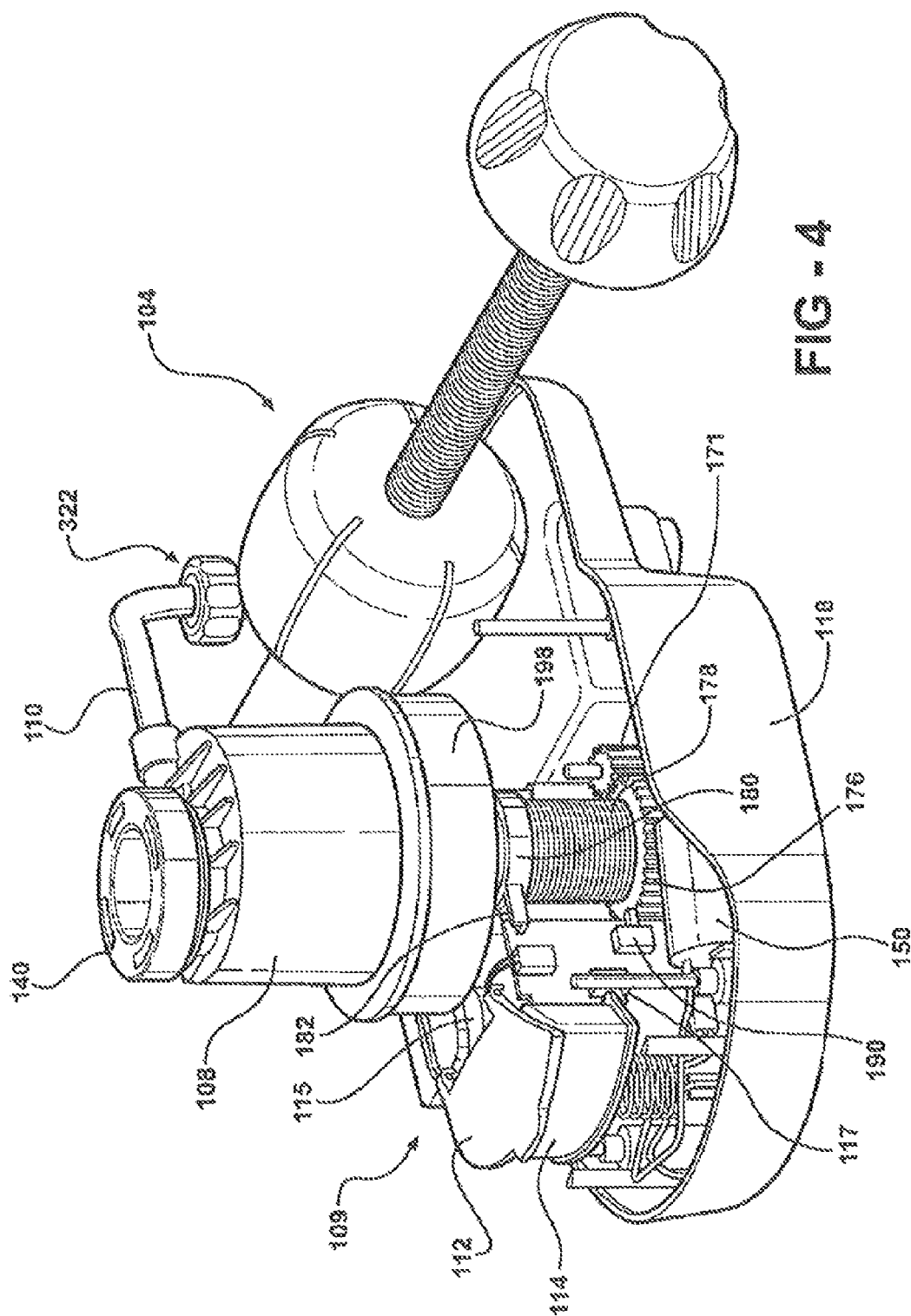
FIG. 4 is a partial front perspective view of the system with a casing and middle housing portion removed to show a motor and transfer mechanism of the mixer.
Figure 5:
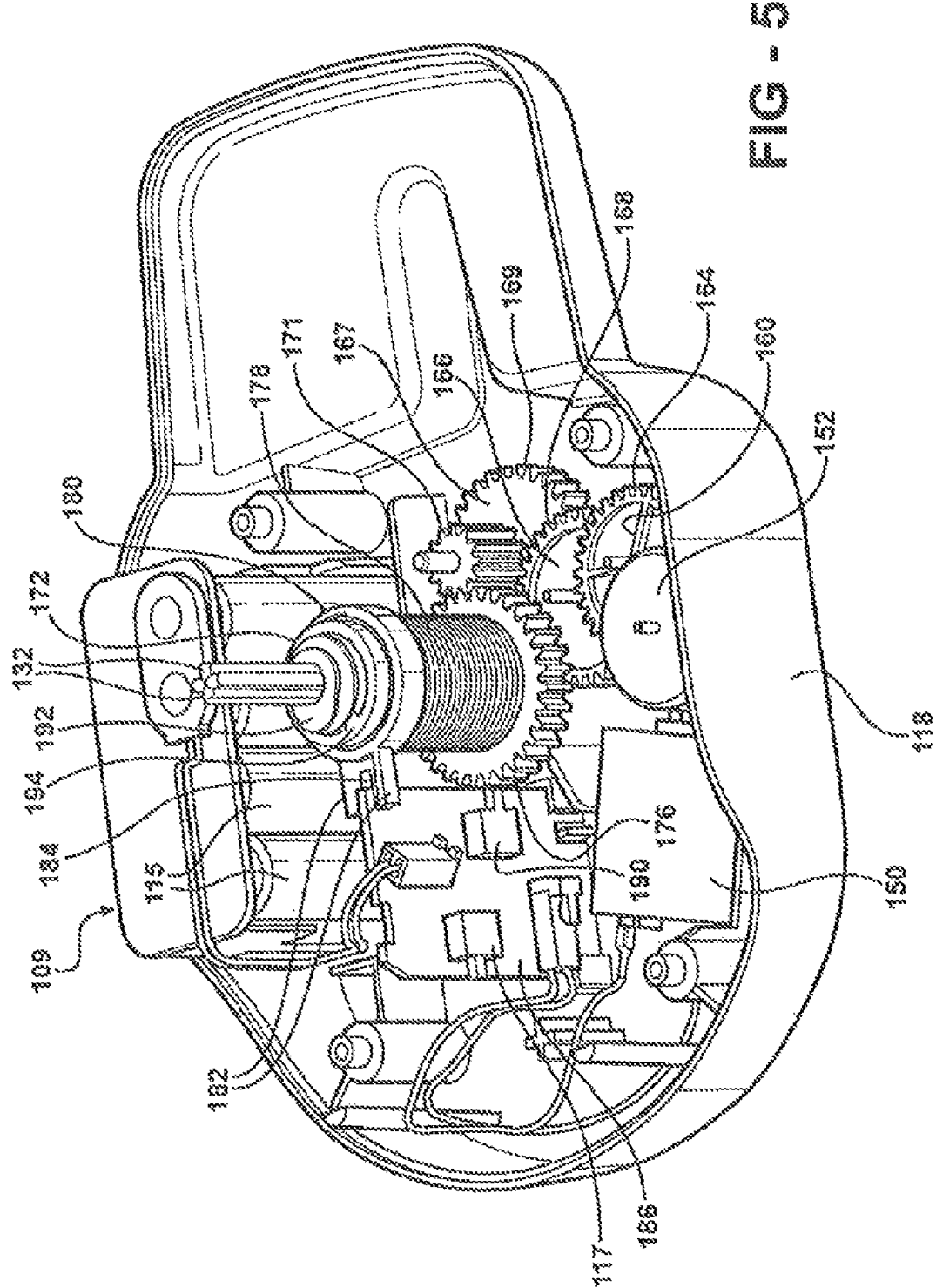
FIG. 5 is a partial top perspective view of a bottom housing portion of the mixer showing a switch and gears of the transfer mechanism.

Referring to FIGS. 4 and 5, the mixer 102 is shown with the casing 107 removed to expose some of its internal components. As shown, the mixer 102 is battery-powered. Batteries 115 are used to power a motor 150 that drives the mixing and transfer operations of the mixer 102. In one embodiment, a battery pack 109 of eight batteries connected in series is used to power the motor 150. The motor 150 is preferably a reversible DC motor such as those available from Mabuchi Motor Co. of Matsudo City, Japan. Possible models that could be used include Model Nos. RC-280RA-2865 and RC-280SA-2865. The mixer 102 is preferably disposable such that the motor 150 and batteries 115 are selected for single use. A switch 117 closes a circuit (not shown) between the batteries 115 and the motor 150 to begin operation of the motor. The switch button 114, when pressed, trips the switch 117 to close the circuit. Once the mixing and transfer operations are complete, the motor 150 ceases to operate.

Figure 6:
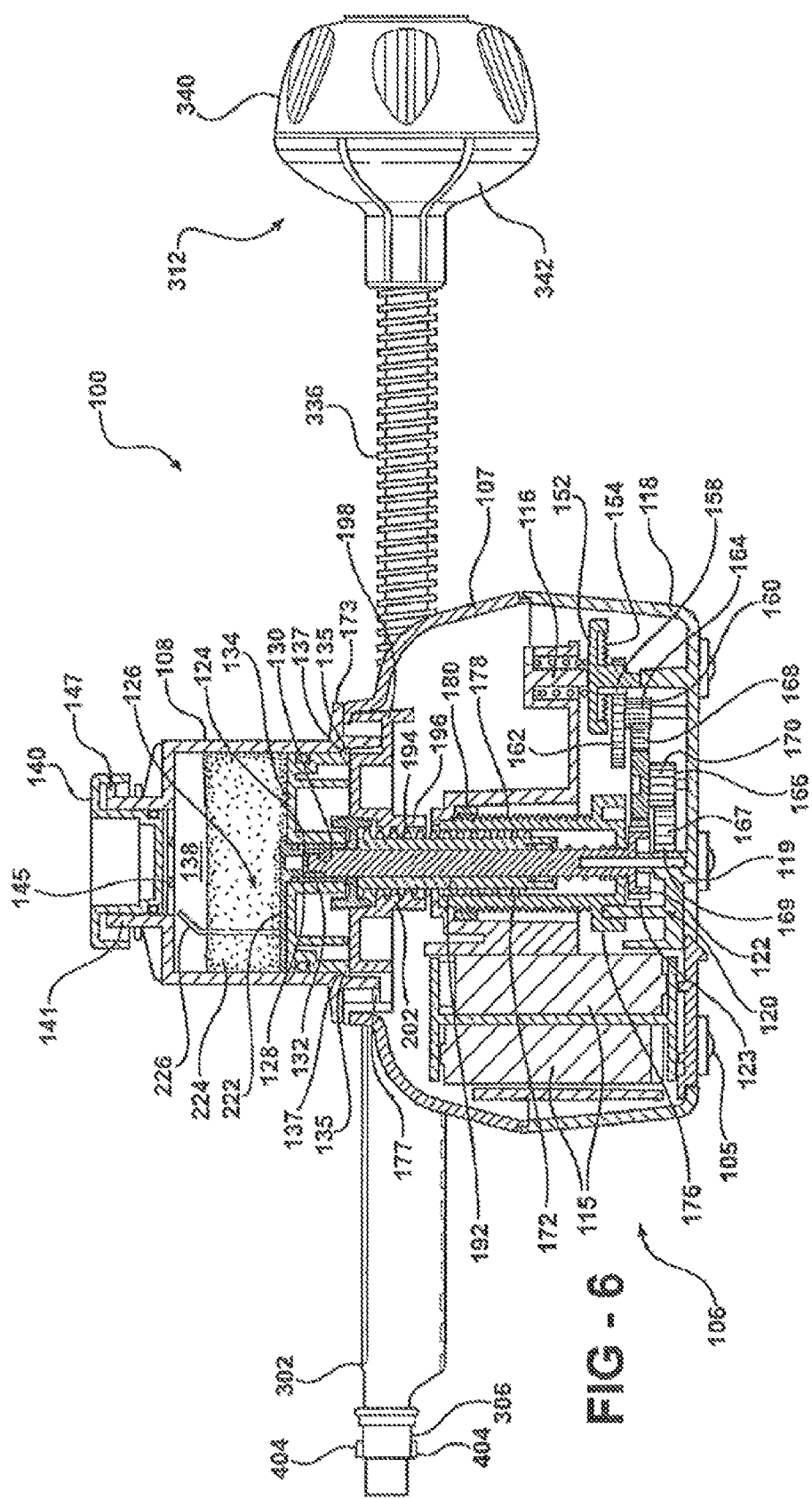
FIG. 6 is a cross-sectional view of the system of FIG. 1 in a mixing phase.
Figure 7:
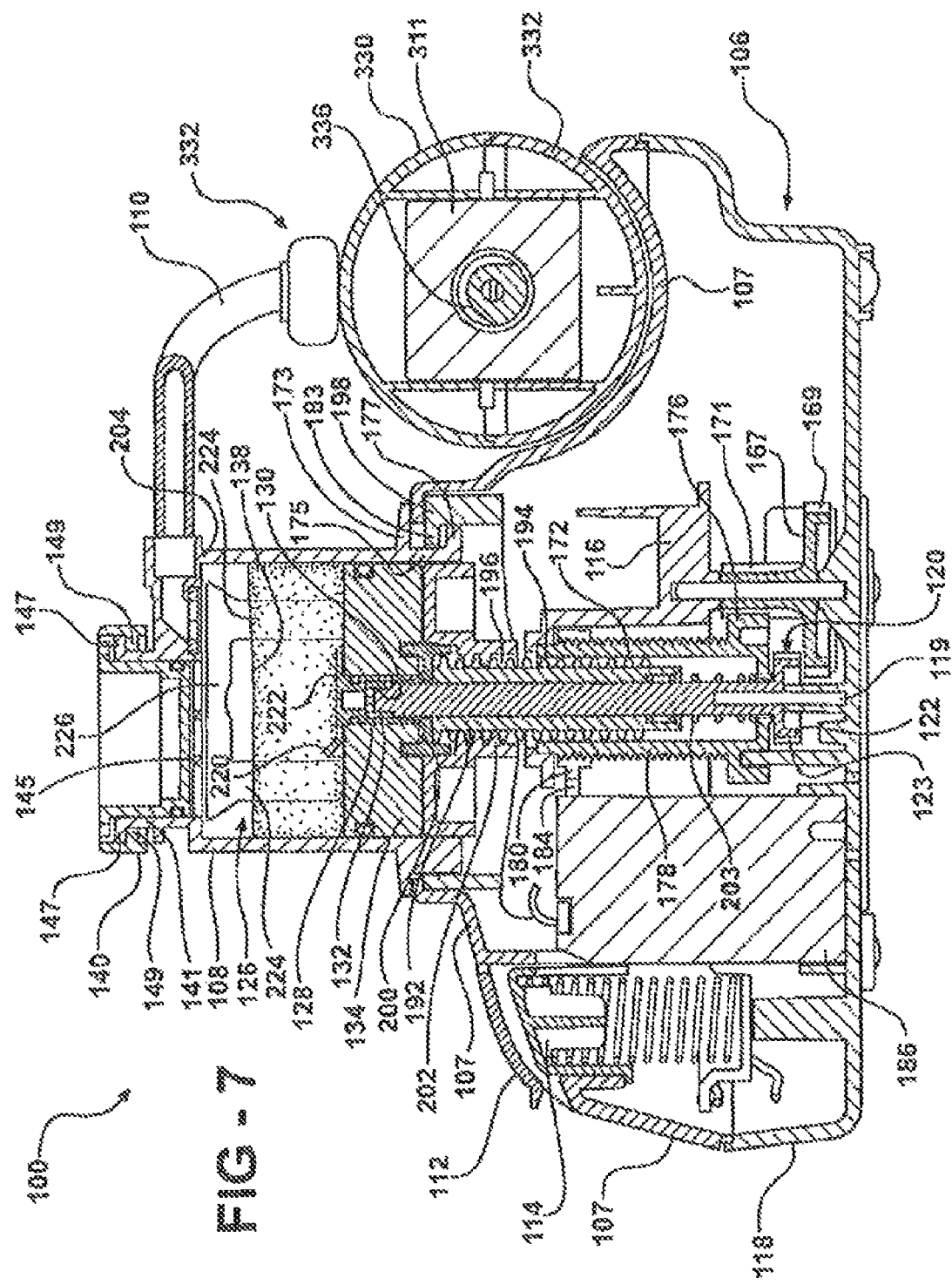
FIG. 7 is another cross-sectional view of the system of FIG. 1 in the mixing phase.
Figure 8:
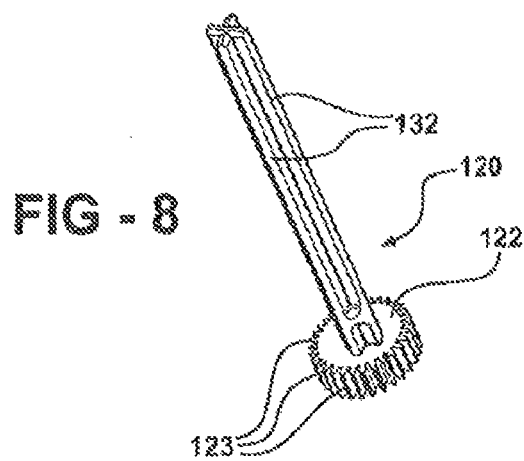
FIG. 8 is a perspective view of a mixing shaft of the mixer.

Referring to FIGS. 6 and 7, the base 106 of the mixer 102 comprises a bottom housing portion 118 and a middle housing portion 116 secured to the bottom housing portion 118 using conventional fasteners, adhesives, and the like. A mixing shaft 120 is rotatably supported between the housing portions 116, 118. The mixing shaft 120 has a mixing gear 122 with mixing gear teeth 123 at one end. The mixing shaft 120 is rotatably supported in the bottom housing portion 118 by a centering pin 119. The mixing shaft 120 extends from the mixing gear end to a second end 124 that is releasably coupled to a mixing paddle 126. This connection is preferably releasable, but could include integral or fixed connections.

Referring to FIGS. 6-10, the mixing paddle 126 includes a hub 128 with inner splines 130 that interact with outer splines 132 on the mixing shaft 120 to rotationally lock the mixing shaft 120 to the mixing paddle 126 during the mixing phase (shown in FIGS. 6 and 7). The outer splines 132 extend along the entire length of the mixing shaft 120 from the mixing gear 122. This rotational locking feature allows the mixing shaft 120 to impart rotational motion to the mixing paddle 126 to adequately mix the bone cement components. When mixing is complete, the rotational lock between the mixing shaft 120 and the hub 128 is removed to prevent further rotation of the mixing paddle 126 in the transfer phase.

Figure 9A:
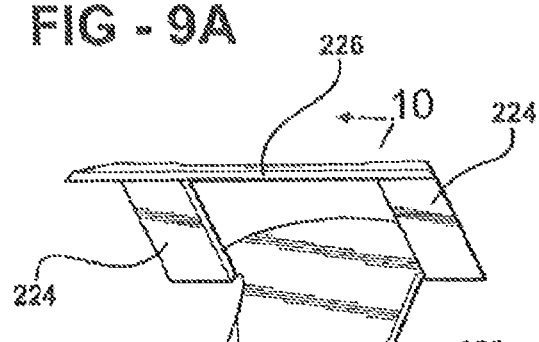
FIGS. 9A and 9B are top perspective views of a mixing paddle of the mixer in normal and flattened states, respectively.
Figure 9B:
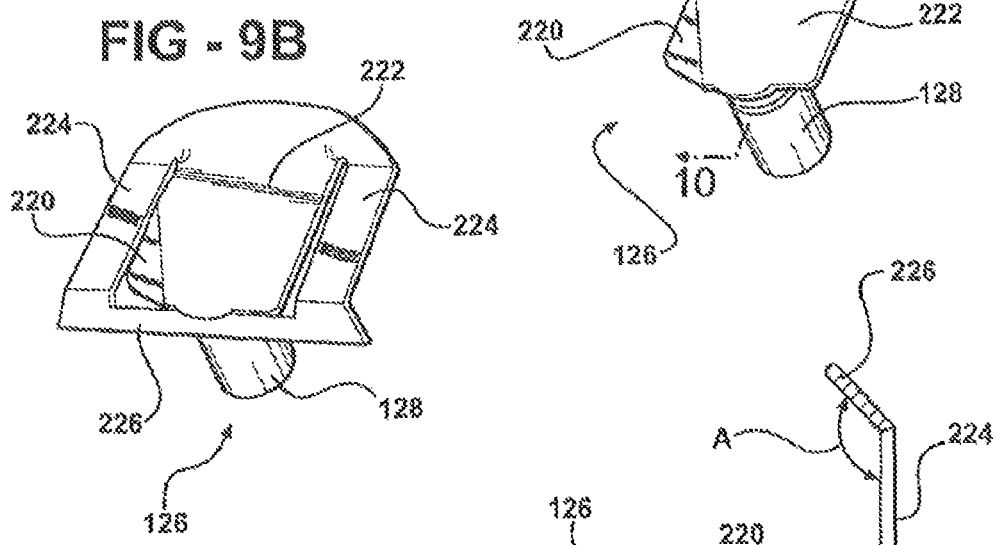
Figure 10:
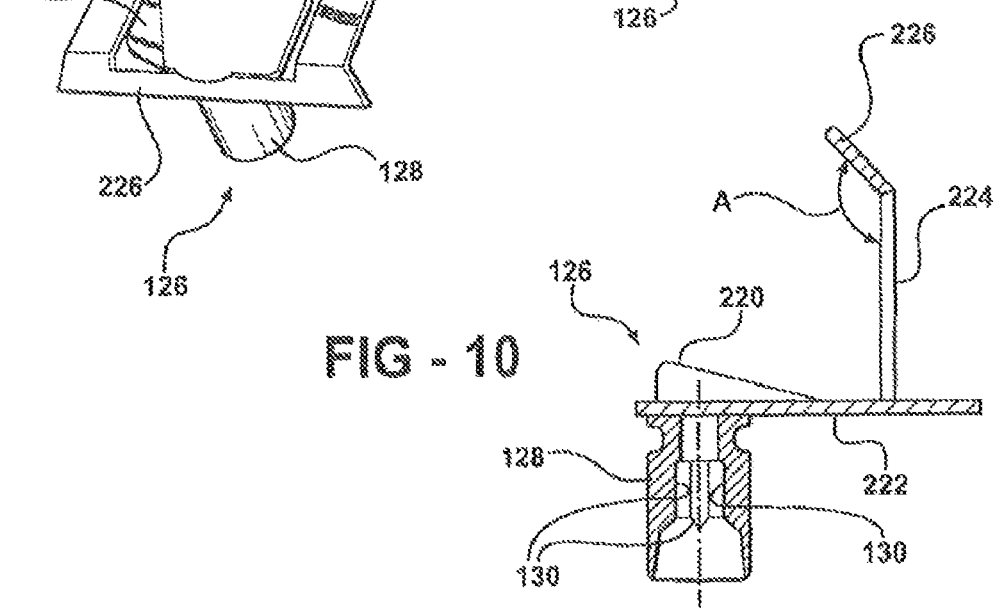
FIG. 10 is a cross-sectional view of the mixing paddle taken generally along the line 10-10 in FIG. 9.
Figure 16:
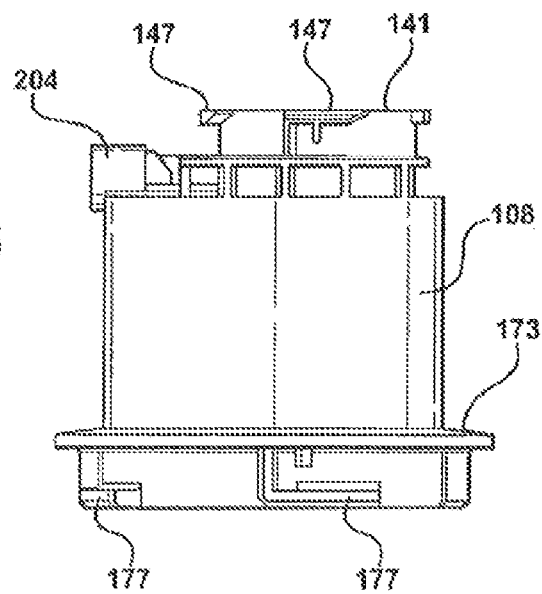
FIG. 16 is a side elevational view of the mixer housing.
Figure 17:
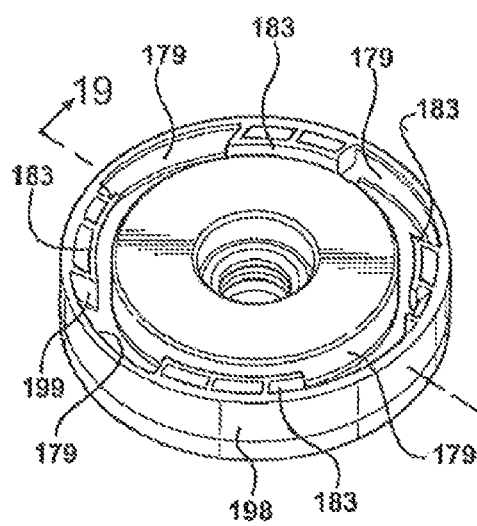
FIG. 17 is a top perspective view of a transfer disc of the mixer.
Figure 18:
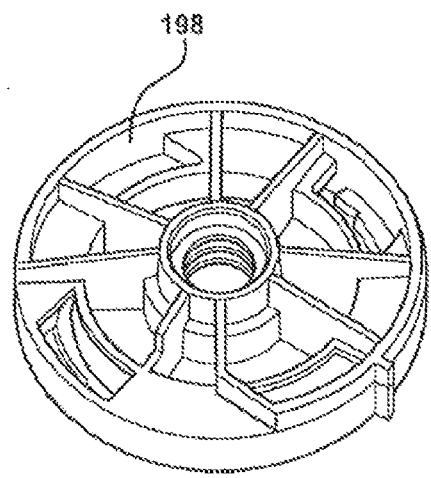
FIG. 18 is a bottom perspective view of the transfer disc.
Figure 19:
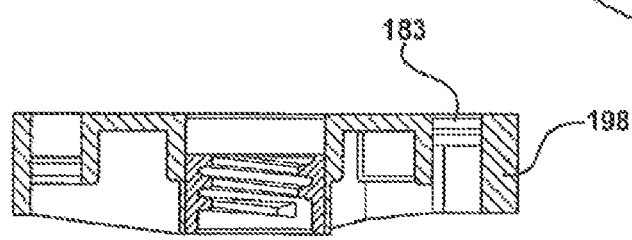
FIG. 19 is a cross-sectional view of the transfer disc taken generally along the line 19-19 in FIG. 17.

The preferred embodiment of the mixing paddle 126 is shown in FIGS. 9A, 9B, and 10. In one embodiment, the mixing paddle 126 is preferably formed from a flat piece of plastic or metal material. The mixing paddle 126 is cut from the flat piece of material and folded/shaped to the configuration shown. The mixing paddle 126 is folded/shaped to include a flat base section 222 and a bent flap 220 forming an obtuse angle with the flat base section 222. The flat base section 222 is fixed to the hub 128 by being integrally molded with the hub 128 or by adhesive or the like. The hub 128 extends downwardly from the flat base section 222. The bent flap 220 is radially spaced from a center of the hub 128. As the mixing paddle 126 rotates, the bent flap 220 urges the bone cement components upwardly. A pair of flat arms 224 extends upwardly from the flat base section 222 generally perpendicularly to the flat base section 222. The flat arms 224 act as mixing vanes to mix the bone cement components.

A flat connector section 226 extends between and connects the flat arms 224. The flat connector section 226 forms an obtuse angle A with the flat arms 224. As a result, when the mixing paddle 126 is urged upwardly in the mixing chamber 138 during the transfer phase (further described below), the flat connector section 226 strikes a top of the mixer housing 108. As the mixing paddle 126 continues to move upwardly in the mixing chamber 138, the mixing paddle 126 begins to compress into a flattened configuration. This includes bending the flat arms 224 downward toward the flat base section 222 about a hinge, then eventually flattening the flat connection section 226 and the bent flap 220 such that they all fall generally in the same plane as the flat base section 222 (see FIG. 9B).

Referring to FIGS. 6-7 and 11-13, a piston 134 rotatably supports the hub 128. More specifically, the hub 128 of the mixing paddle 126 is seated in a bore 136 defined through the piston 134. An o-ring seals the hub 128 in the bore 136. The piston 134 is releasably secured in the mixer housing 108. Another o-ring seals the piston 134 to an interior surface of the mixer housing 108. The piston 134 includes a pair of flexible tabs 135 that rest beneath a shoulder 137 defined in the interior surface of the mixer housing 108. The flexible tabs 135 hold the piston 134 in place until such time as the piston 134 is forced upwardly to transfer the mixture to the delivery device 104. At that point, the flexible tabs 135 are forced inwardly to allow the piston 134 to move upwardly along the interior surface of the mixer housing 108. In the mixing phase, however, the piston 134 remains in place and forms a mixing chamber 138 with the mixer housing 108.

In one embodiment, the mixer 102 may be shipped with a powder component of the bone cement stored in the mixing chamber 138. In this embodiment, a cap 140 is releasably coupled to the mixer housing 108 during shipment to keep the powder component in the mixing chamber 138. More specifically, the cap 140 is secured to a cylindrically-shaped top port 141 of the mixer housing 108.

The top port 141 defines a pour opening 143 (see FIG. 14) that enters the mixing chamber 138 through a plurality of web sections 145 that form a web. A plurality of port flanges 147 extends radially outwardly from the top port 141 to engage the cap 140. The cap 140 includes a plurality of locking tabs 149 that engage the port flanges 147 to lock the cap 140 to the mixer housing 108. An o-ring seals the cap 140 to the mixer housing 108. When the system 100 is ready to be used, the user removes the cap 140 to add a monomer component of the bone cement through the pour opening 143 to the powder component already placed in the mixing chamber 138 or also added through the pour opening 143. Once the bone cement components are disposed in the mixing chamber 138, the mixer 102 is ready for operation.

The motor 150 operates through a gear arrangement to rotate the mixing shaft 120 during the mixing phase to mix the powder and monomer components. Rotation of the mixing shaft 120 imparts rotation to the mixing paddle 126, which is disposed in the mixing chamber. The gear arrangement includes a face gear 152 having a set of face gear teeth 154. A pinion gear 156 (see FIG. 22) is fixed to a shaft of the motor 150 to rotate with the motor 150 during operation. The pinion gear 156 has pinion gear teeth 157 engaging the face gear teeth 154 such that the motor 150 drives the face gear 152 during operation.

The face gear 152 drives a first spur gear 160, which drives a second spur gear 166. More specifically, the face gear 152 has a lower set of gear teeth 158 continuously engaging an upper set of spur gear teeth 162 formed on the first spur gear 160. A lower set of spur gear teeth 164 formed on the first spur gear 160 continuously engages an upper set of spur gear teeth 168 formed on the second spur gear 166. The upper set of spur gear teeth 168 engages the mixing gear teeth 123 to rotate the mixing shaft 120 and mixing paddle 126 during the mixing phase.

The second spur gear 166 drives a third spur gear 167. In particular, a lower set of spur gear teeth 170 formed on the second spur gear 166 engages a lower set of spur gear teeth 169 formed on the third spur gear 167. The third spur gear 167 also includes an upper set of spur gear teeth 171. The upper set of spur gear teeth 171 formed on the third spur gear 167 engages a set of transfer gear teeth 176 formed on a transfer gear 172. As a result, when the motor 150 operates, both the mixing shaft 120 and the transfer gear 172 rotate. Each of the face gear 152 and spur gears 160, 166, 167 are supported by centering pins captured between the middle housing portion 116 and the bottom housing portion 118.

The transfer gear 172 is generally cylindrical and includes a first open end and a second, partially closed, end defining an aperture. The mixing shaft 120 is rotatably supported in the aperture and passes through the cavity such that rotation of the mixing shaft 120 does not interfere with rotation of the transfer gear 172. The speed with which the mixing shaft 120 and transfer gear 172 rotate depends on the gear ratios of the gears. In some embodiments, the transfer gear 172 rotates much slower than the mixing shaft 120.

The transfer gear 172 forms part of a transfer mechanism of the mixer 102. Transfer threads 178 are defined on an outer surface of the transfer gear 172. The transfer mechanism also includes a switch nut 180 threaded on the transfer gear 172. The switch nut 180 does not rotate so that as the transfer gear 172 rotates, the switch nut 180 moves downwardly along the transfer gear 172. The switch nut 180 has two projections 182 with a notch 184 defined therebetween. The notch 184 rides along an edge of a printed circuit board 186 fixed to the bottom housing 118 to prevent rotation of the switch nut 180 with the transfer gear 172. In other words, the edge of the printed circuit board 186 rides in the notch 184 between the projections 182 as the transfer gear 172 rotates thereby preventing the switch nut 180 from rotating. The motor 150, by way of its rotation of the transfer gear 172, operatively engages the switch nut 180. This is best shown in FIG. 5.

During operation, after the switch 117 has been closed, the switch nut 180 rides downwardly along the printed circuit board 186 as it further threads onto the transfer gear 172 in one direction until it engages a switch 190 (see FIG. 5), which when tripped by movement of the switch nut 180, opens the circuit between the batteries 115 and the motor 150 to shut down operation of the motor 150. Thus, the switch 117 and the switch 190 act as three-way switches such that both are able to open/close the circuit between the batteries 115 and the motor 150.

The transfer mechanism further includes a driver 192 that is keyed to the transfer gear 172 to rotate with the transfer gear 172. Thus, the transfer gear 172 operatively couples the motor 150 to the driver 192. The driver 192 includes a pair of keyways 193 (see FIG. 22), while the transfer gear 172 includes a pair of keys 195 (see FIG. 22) slidably disposed in the keyways 193. The driver 192 is free to move axially relative to the transfer gear 172. The driver 192 has driving threads 194 defined on its outer surface. During the mixing phase, the driving threads 194 are rotatably received in a bore 196 of a transfer disc 198. The transfer disc 198 is coupled to a bottom of the mixer housing 108 and fixed from movement. The transfer disc 198 also forms part of the transfer mechanism and acts as a drive nut 198 for the driver 192.

During the mixing phase, the driving threads 194 rotate within the bore 196 of the transfer disc 198 and engage corresponding threads 202 in the bore 196. Thus, the transfer disc 198 operates as a fixed drive nut. The threads 202 are configured such that the driving threads 194 advance slowly during the mixing phase. FIGS. 6 and 7 show the driving threads 194 fully advanced through the bore 196. This represents the end of the mixing phase. A spring 203 biases the driver 192 upwardly in the cavity of the transfer gear 172 to facilitate engagement with the threads 202. The time required for the driving threads 194 to fully advance through the bore 196 represents the mixing phase. In other words, a predetermined mixing period is set by the amount of time it takes for the driving threads 194 to fully advance through the transfer disc 198. Once the driving threads 194 completely pass through the bore 196, the transfer phase begins. The transfer phase continues for a predetermined transfer period, which is defined between the start of transfer and the actuation of the second switch 190, which ceases operation of the motor 150.

Figure 20:
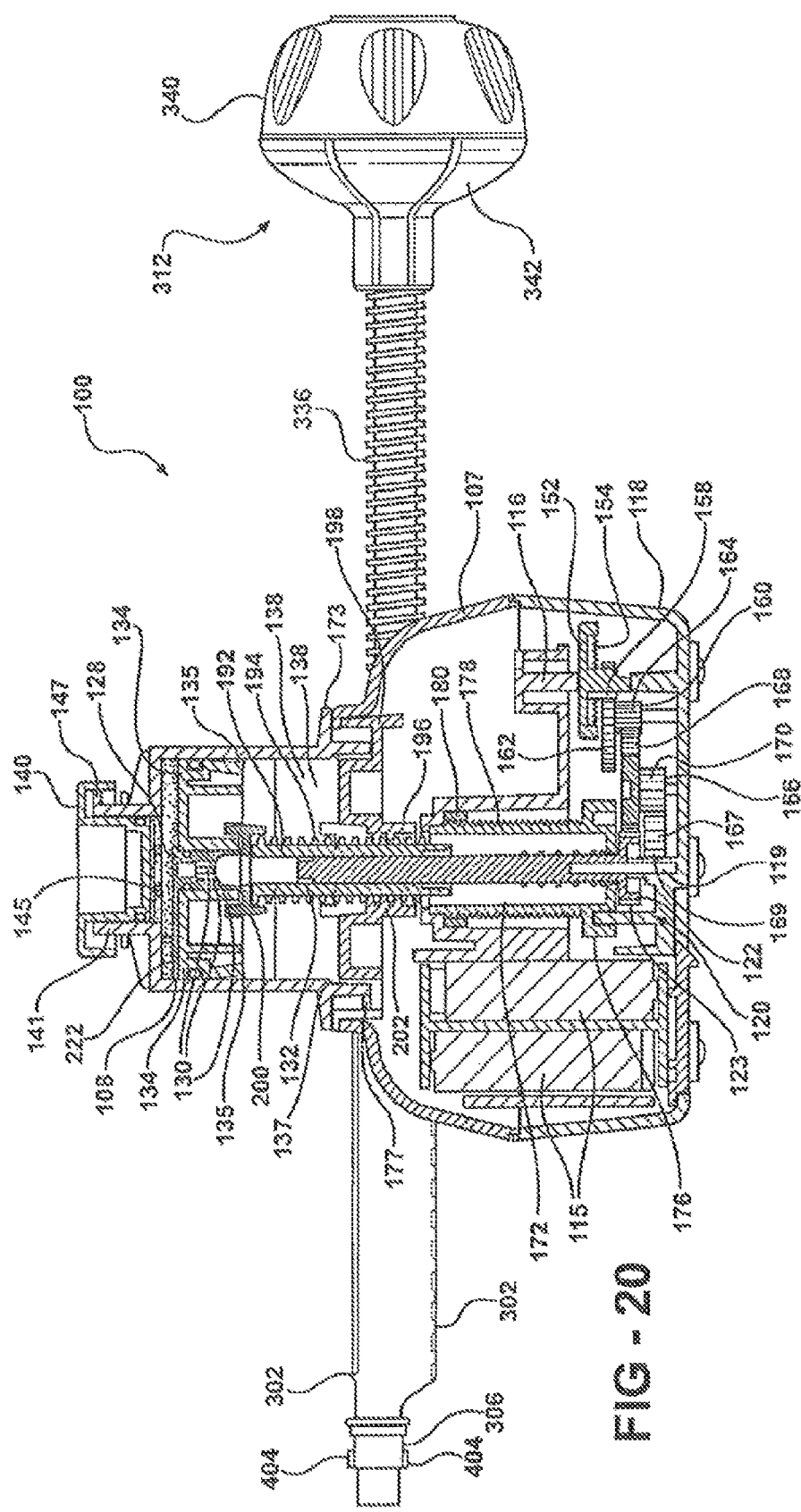
FIG. 20 is a cross-sectional view of the system of FIG. 1 in a transfer phase.
Figure 21:
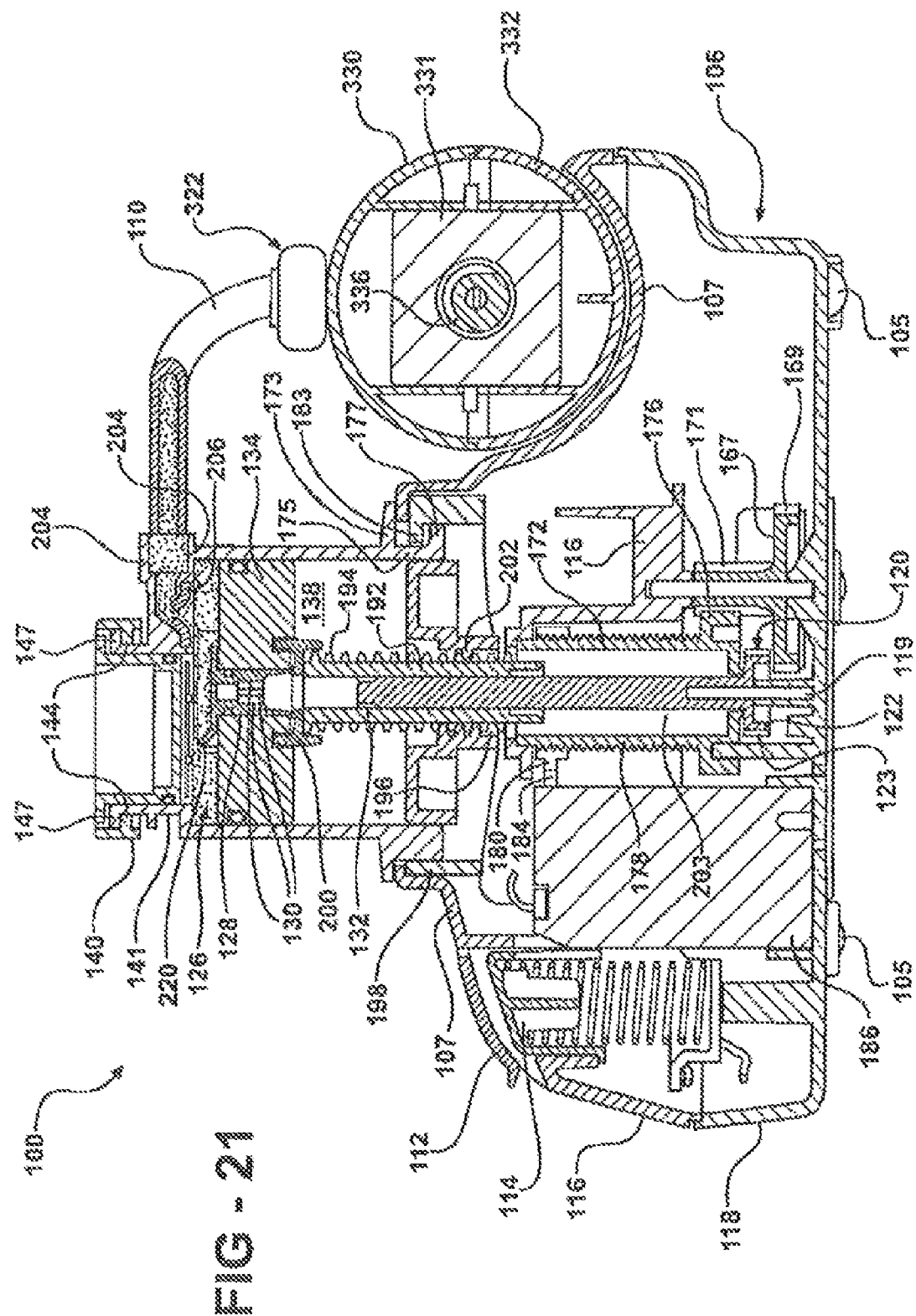
FIG. 21 is another cross-sectional view of the system of FIG. 1 in the transfer phase.

Referring to FIGS. 20 and 21, when the driver 192 advances in the transfer phase, it pushes the push cap 200 axially upwardly against the piston 134, which in turn urges the piston 134 upwardly through the mixing chamber 138. As a result, the bone cement mixture is urged upwardly through an exit port 204 to the transfer conduit 110 and into the delivery device 104. A one-way valve 206 is arranged in the exit port 204 to prevent the re-entry of the bone cement mixture once it exits the mixer 102. As the piston 134 rises in the mixing chamber 138, the mixing paddle 126 folds down to a compact size to permit a majority of the bone cement mixture to be pressed out of the mixing chamber 138 and into the delivery device 104.

The motor operates through the gear arrangement to rotate the mixing shaft 120 and actuate the mixing paddle 126 during the mixing phase to mix the powder and liquid components, while also rotating the transfer gear 172 to actuate the transfer mechanism to automatically transfer the mixture from the mixing chamber 138 to the delivery chamber of the delivery device 104 after the predetermined mixing period has elapsed. In other words, the motor 150 operatively engages both the mixing shaft 120 and the transfer mechanism (including the transfer gear 172, driver 192, piston 134, etc.). The motor 150 continues operation from its start, upon actuation of the switch 117, until it stops upon actuation of the second switch 190, during which time the motor 150 operates to mix the components in the mixer 102 and transfer the mixture to the delivery device 104. In one embodiment, the switch 117 and the second switch 190 are combined into a single switch (not shown) that is closed to start operation of the motor 150 by an actuator, and opened to stop operation of the motor 150.

In still other embodiments, the switch 190 reverses the polarity of the motor 150 and causes the transfer gear 172 to reverse its rotation. Consequently, the switch nut 180 changes direction and rides back upwardly along the printed circuit board 186. In this embodiment, the threads 202 are configured such that during the mixing phase the driving threads 194 cannot engage the threads 202 of the transfer disc 198. However, when the polarity switch 190 is tripped by the switch nut 180, the driver 192 reverses its direction of rotation with the transfer gear 172 and engages the threads 202 in a manner that advances the driver 192 axially during the transfer phase. In this embodiment, a third switch (not shown) or other mechanism would be required to be tripped by the switch nut 180 as it travels back upwardly along the printed circuit board 186 to stop operation of the motor 150.

As shown in FIGS. 7 and 14-19, the bottom of the mixer housing 108 includes a flange 173 and a short wall 175 extending downwardly from the flange 173. A plurality of locking tabs 177 (see FIG. 15) are spaced circumferentially about the short wall 175 and extend radially outwardly from the short wall 175. During assembly of the mixer 102, the locking tabs 177 are inserted into openings 179 (see FIG. 17) defined in a top of the transfer disc 198. The casing 107 is captured between the mixer housing 108 and the transfer disc 198 when this is done (see FIG. 21). The mixer housing 108 is then rotated one-quarter turn such that the locking tabs 177 slide beneath corresponding locking members 183 on the transfer disc 198 until they reach stops 199. The piston 134 rests on top of the transfer disc 198 and is initially coupled to the transfer disc 198 by the push cap 200.

Figure 22:
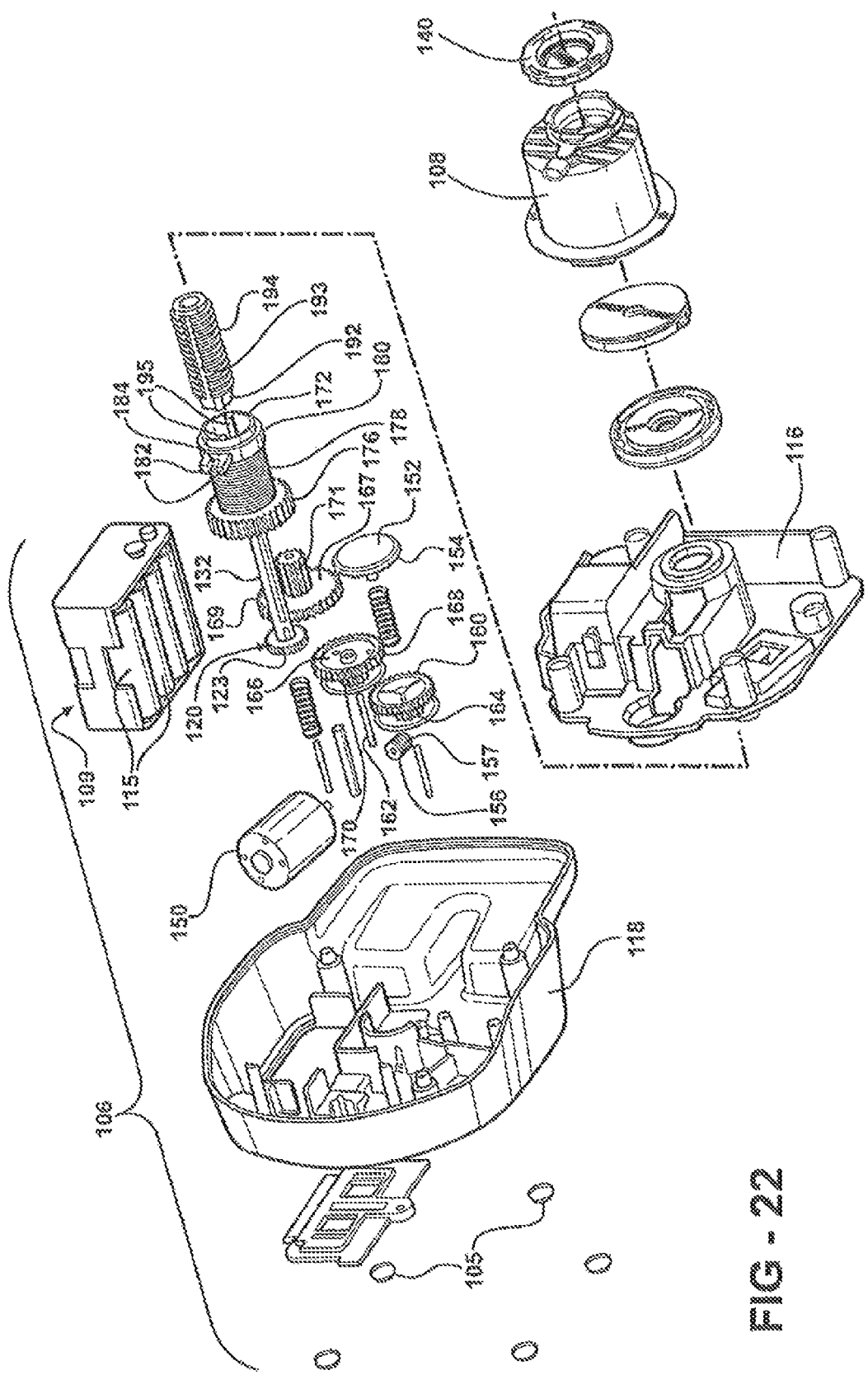
FIG. 22 is an exploded view of a base of the mixer.

FIG. 22 illustrates an exploded view of the base 106 including the bottom housing portion 118, the middle housing portion 116, and the gear arrangement disposed therebetween for converting motor operation into mixing and transfer operations. FIG. 23 shows the base 106 fully assembled.

FIGS. 24-29 illustrate perspective views of the transfer gear 172, the driver 192, the switch nut 180, the first spur gear 160, the second spur gear 166, and the third spur gear 167.

Figure 30:
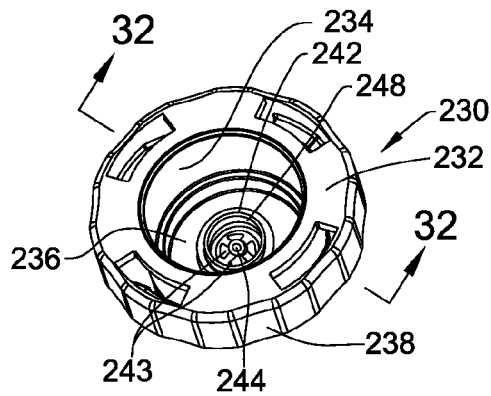
FIG. 30 is a top perspective view of a cap of the mixer.
Figure 31:
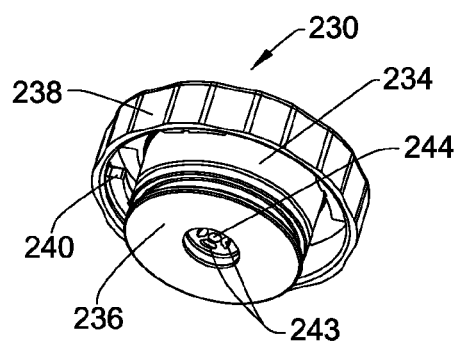
FIG. 31 is a bottom perspective view of the cap.
Figure 32:
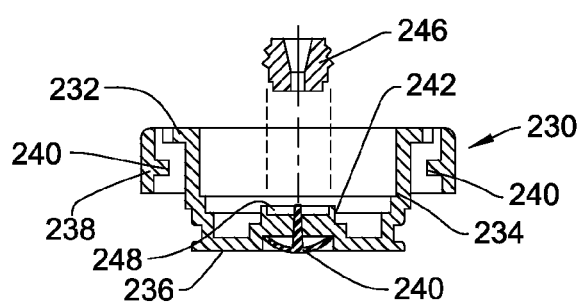
FIG. 32 is a cross-sectional view of the cap taken generally along the line 32-32 in FIG. 30 illustrating an optional umbrella valve and luer-lock fitting that can be used with the cap.

Referring to FIGS. 30-32, the cap 230 is shown. The cap 230 includes a top 232. A cap wall 234 is disposed on the top 232 and extends downwardly from the top 232 to a bottom wall 236. A gripping flange 238 extends downwardly from the top 232 and is spaced from the cap wall 234. A plurality of locking tabs 240 are disposed on the gripping flange 238 and extend radially inwardly into a gap between the gripping flange 238 and the cap wall 234. The locking tabs engage the tabs 147 on the top port 141.

A boss 242 protrudes upwardly from the bottom wall 236. The boss 242 defines a plurality of openings 243 and a central bore 244 through the bottom wall 236. A luer-lock fitting 246 sits in a seat 248 defined in the boss 242. An umbrella valve 250 is seated in the central bore 244. The luer-lock fitting 246 and umbrella valve 250 are used to receive units that inject liquid monomer into the mixing chamber 138 without requiring removal of the cap 230. The monomer is injected through the openings 243, which opens the umbrella valve 250. Once injected, the umbrella valve 250 closes and prevents odors from escaping the mixing chamber 138.

Figure 33:
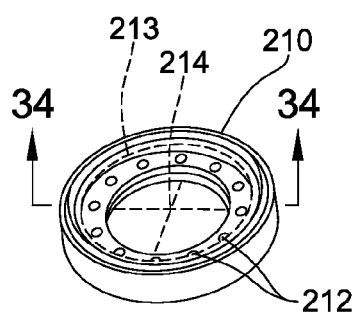
FIG. 33 is a top perspective view of a valve ring of the mixer.
Figure 34:
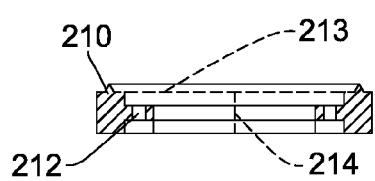
FIG. 34 is a cross-sectional view of the valve ring taken generally along the line 34-34 in FIG. 32.
Figures 35A, 35B:
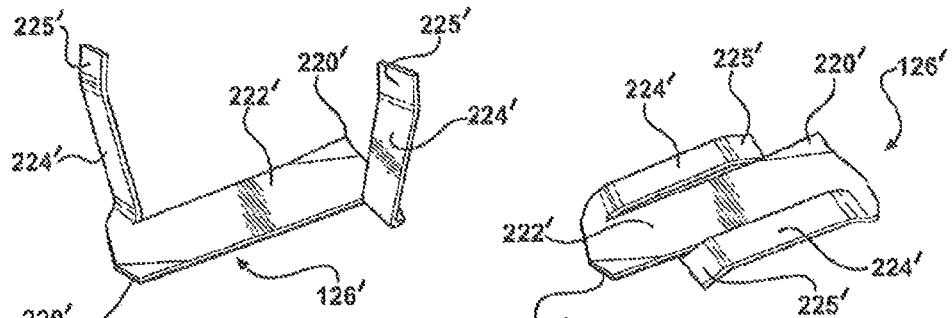
Figures 36A, 36B:
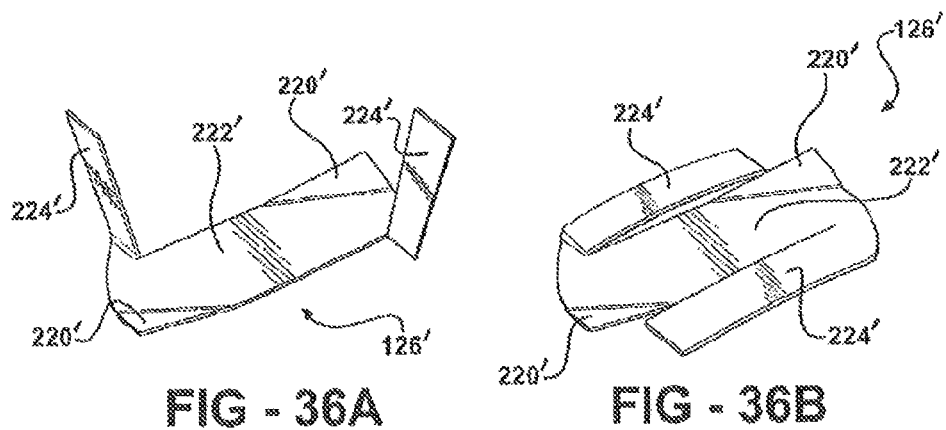
Figures 37A, 37B:
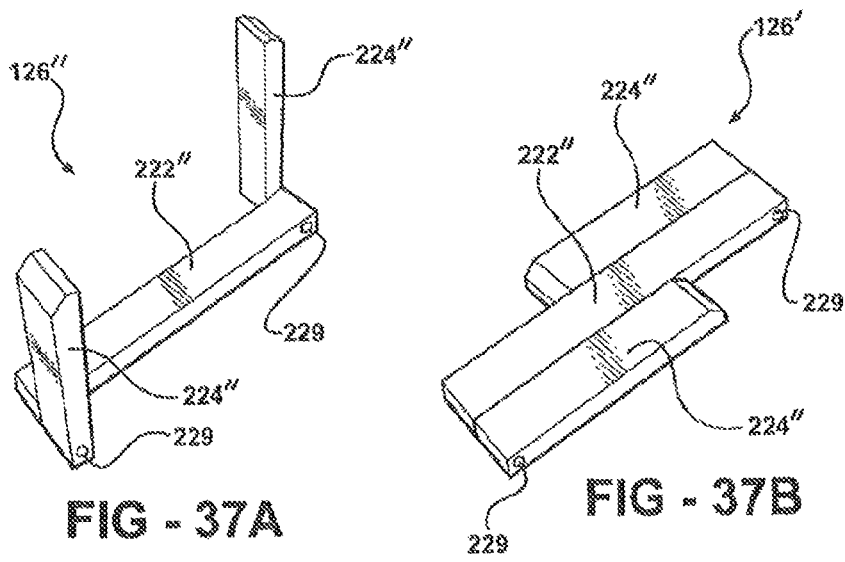

Referring to FIGS. 33 and 34, the one-way valve inserted into the exit port 204 is shown in more detail. Referring to FIG. 31, the valve includes a metal ring 210 having a plurality of apertures 212 for receiving an elastomeric material 213 in a molding process. The material 213 fills in the apertures 212 as shown in FIG. 33 and includes cross-cut slits 214 that remain closed in the mixing phase, but open up and allow the mixture to flow therethrough into the transfer conduit 110 during the transfer phase.

Alternative embodiments of the mixing paddle 126 are shown in FIGS. 35A-38B. In FIGS. 35A-36B, the mixing paddle 126' is formed of plastic and includes a pair of flat arms 224' extending upwardly from a flat base section 222'. A pair of opposed bent flaps 220' form an obtuse angle with the flat base section 222'. In this embodiment, the flat arms 224' are opposed from one another on opposite sides of a center of the mixing paddle 126'. The flat arms 224' further include bent ends 225' that strike the top of the mixer housing 208 in the transfer phase and bend inwardly to flatten the flat arms 224'.

Referring to FIGS. 35A-37B, the mixing paddle 126' is formed of metal such as aluminum.

In FIGS. 38A and 38B, a mixing paddle 126" has a pair of opposed arms 224" that are pivotally connected to a flat base section 222" by a pair of pivot pins 229.

In FIG. 39, a mixing paddle 126''' includes a flat base section 222''', a bent flap 220''' forming an obtuse angle with the flat base section 222''', and a single flat arm 224''' extending upwardly generally perpendicularly to the flat base section 222'''. An extension 231 extends at an obtuse angle for crossing the mixing chamber 138.

The mixer housing 108, transfer disc 198, mixing shaft 120, transfer gear 172, face gear 152, spur gears 160, 166, 167, switch nut 180, driver 192, piston 134, cap 140, mixing paddle 126, bottom housing portion 118, middle housing portion 116, casing 107, and switch cover 112 are preferably formed of a bio-compatible plastic material such as nylon, PBT (polybutylene terephthalate), PC (polycarbonate), ABS (acrylonitrile butadiene styrene), glass-filled nylon, glass-filled polyetherimide, or the like.

II. Delivery Device

Referring to FIGS. 39-42, the delivery device 104 is shown. The delivery device 104 comprises a reservoir 302 for receiving the bone cement mixture from the transfer conduit 110 during the transfer phase. The reservoir 302 includes an entry port 314 defined in a sidewall of the reservoir 302. A valve housing 316 (see also FIG. 42) is outfitted with an o-ring 318 and is seated in the entry port 314. The valve housing includes a plurality of flow paths 319 and a central bore 321. As shown in FIG. 41, a one-way umbrella valve 320 is supported in the central bore 321 of the valve housing 316 such that the bone cement mixture opens the valve 320 to fill the reservoir 302. The one-way umbrella valve 320 prevents the bone cement mixture from re-entering the mixer 102. A handle 304 is mounted about the reservoir 302 for grasping by the user.

A rotatable fitting 322 is locked in the valve housing 316 during the mixing and delivery phases. To accomplish this, the rotatable fitting 322 fits through an aperture 325 in the handle 304. The rotatably fitting 322 includes a pair of diametrically opposed locking tabs 306 that engages the handle 304. The handle 304 includes a plurality of locking flanges 327 spaced circumferentially from one another in the aperture 325. The locking flanges 327 extend radially inwardly into the aperture 325. During assembly, the locking tabs 306 pass into the aperture 325 between the locking flanges 327 and are rotated into place with the locking tabs 306 beneath the locking flanges 327. An annular flange 329 of the rotatable fitting 322 rests on top of the locking flanges 327 when in position (see FIG. 41).

One end of the transfer conduit 110 fits into the rotatable fitting 322. A throughbore 331 is defined through the rotatable fitting 322 to transfer the bone cement mixture to the reservoir 302 from the transfer conduit 110. During transfer the bone cement mixture passes through the throughbore 331 under pressure thereby opening the one-way umbrella valve 320 and passing through the flow paths 319 (see FIG. 42) into the reservoir 302. Once transfer is complete, the rotatable fitting 322 is rotated counterclockwise to release the rotatable fitting 322 from the valve housing 316 thereby allowing the user to remove the delivery device 104 from its cradle mounts 333 on the mixer 102 in preparation for delivering the bone cement mixture to the target site.

A nut 324 is mounted to a proximal end of the reservoir 302. In particular, the proximal end of the reservoir 302 has a rectangular flange 326 for supporting the nut 324. The rectangular flange 326 slides into a slot 328 defined in the nut 324. The nut 324 has a generally box-like shape that is secured between two halves 330, 332 of the handle 304. Each half 330, 332 of the handle 304 has a complimentary box-shaped cavity 334 such that the nut 324 fits snugly in the cavities 334 when the halves 330, 332 are fixed together. The halves 330, 332 may be fixed together by conventional fasteners, adhesives, and the like.

Figure 40:
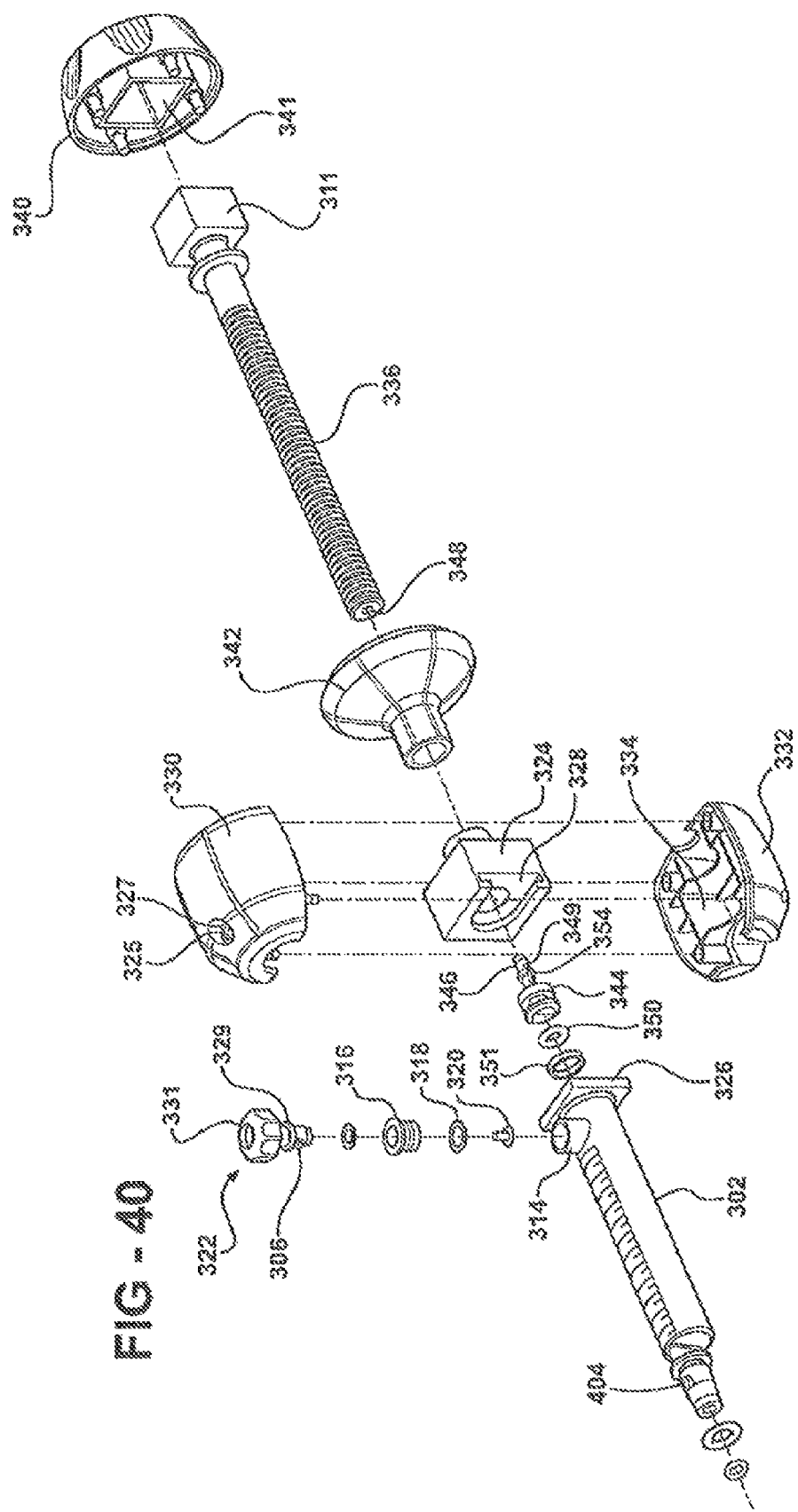
FIG. 40 is an exploded perspective view of the delivery device.

A plunger 310 drives the mixture through the reservoir 302 during delivery. The plunger 310 includes a threaded shaft 336 that engages threads 338 of the nut 324. A plunger head 344 is snap-fit to the threaded shaft 336 to form a distal end of the plunger 310. The plunger head 344 is snap-fit to the threaded shaft 336 by inserting a stem 346 of the plunger head 344 into a bore 348 defined through the threaded shaft 336. Referring to FIGS. 40 and 41, the stem 346 has a pair of diametrically opposed detent ramps 354 that slide through the bore 348 in a compressed configuration (by being pressed together via a slot 349 defined through the stem 346) until the ramps 354 pass a shoulder 356 in the bore 348. Once they pass the shoulder 356, the ramps 354 spring outwardly to engage the shoulder 356 and prevent withdrawal of the plunger head 344. An o-ring 350 is seated with a dynamic seal 351 in an outer groove defined in the plunger head 344 to seal against an interior of the reservoir 302.

A proximal end 311 of the plunger 310 has a generally box-like shape. A knob 312 is mounted about the proximal end 311 of the plunger 310 to facilitate rotation of the plunger 310. The knob 312 has a proximal knob portion 340 defining a box-shaped cavity 341 for receiving the proximal end 311 of the plunger 310 such that as the user rotates the proximal knob portion 340, the plunger 310 also rotates. A distal knob portion 342 is fastened to the proximal knob portion 340 using fasteners, adhesives, or the like. The proximal end 311 of the plunger 310 is captured between the proximal 340 and distal 342 knob portions to prevent the proximal end 311 of the plunger 310 from slipping out of the box-shaped cavity 341.

Figure 43:
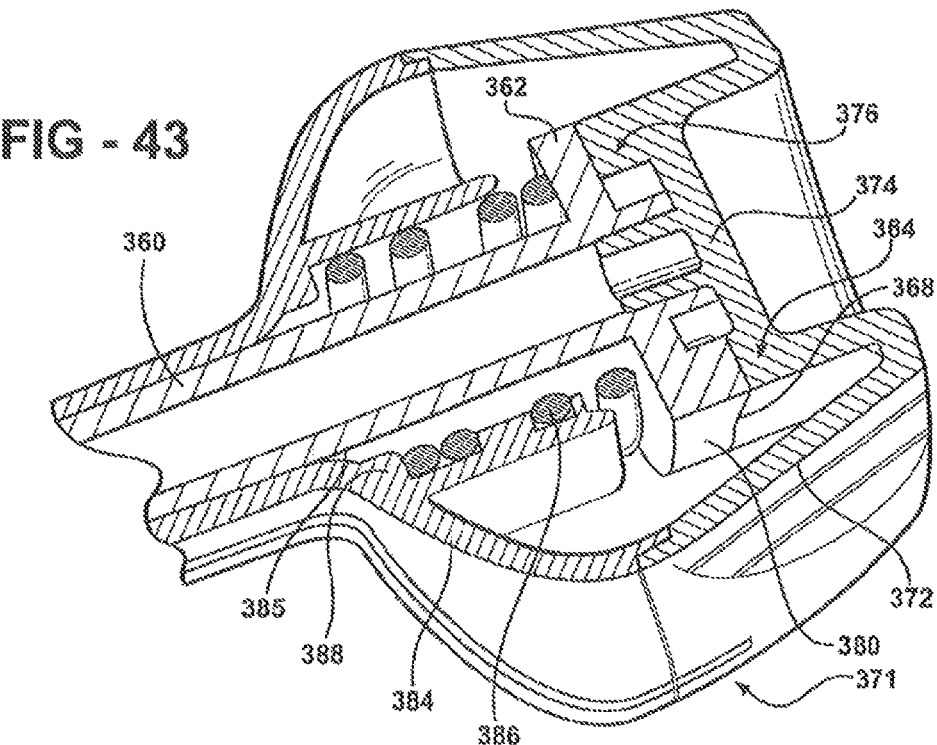
FIG. 43 is a partial cross-sectional perspective view illustrating an optional clutch mechanism of the delivery device.
Figure 44:
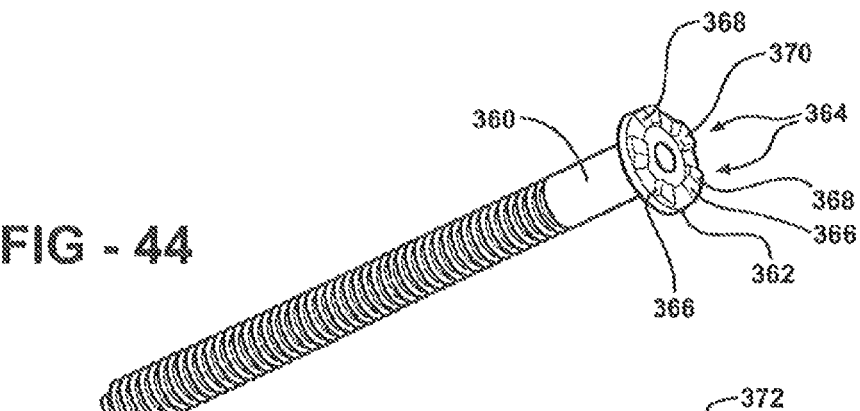
FIG. 44 is a top perspective view of an alternative plunger of the delivery device.
Figure 45:
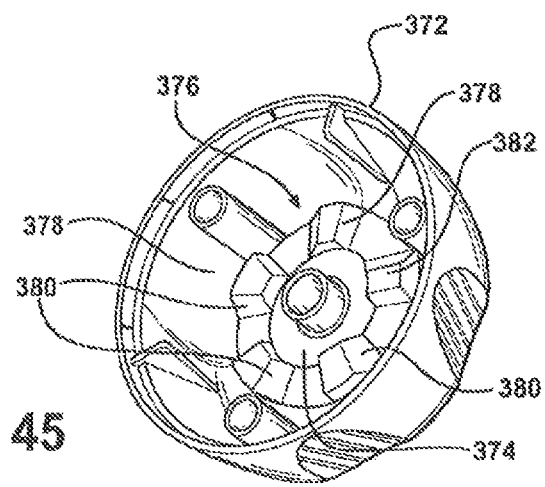
FIG. 45 is a bottom perspective view of an alternative proximal knob portion of the delivery device.

Referring to FIGS. 43-45, an alternative plunger shaft 360 is shown. Referring specifically to FIG. 44, a proximal end of the plunger shaft 360 includes a flange 362 and a plurality of projections 364 disposed on the flange 362. The plurality of projections 364 extend proximally from the flange 362. The projections 364 are circumferentially spaced from one another about a periphery of the flange 362. Each of the projections 364 has a vertical surface 366 and an angled surface 368 (forms acute angle with flange 362) meeting at a plateau 370 generally parallel to the flange 362. In the embodiment, a knob 371 is mounted to the proximal end of the plunger shaft 360 to facilitate rotation of the plunger shaft 360. The knob 371 includes a proximal knob portion 372. The proximal knob portion 372 includes a top 374 and a plurality of complimentary projections 376 disposed on the top 374 and extending distally from the top 374. The complimentary projections 376 mate with the projections 364 on the flange 362 by fitting in spaces defined between the projections 364 on the flange 362.

Each of the complimentary projections 376 also include a vertical surface 378 and an angled surface 380 meeting at a plateau 382 generally parallel to the top 374. A distal knob portion 384 is fastened to the proximal knob portion 372 using fasteners, adhesives, or the like. The proximal end of the plunger shaft 360 is captured between the proximal 372 and distal 384 knob portions. The plunger shaft 360 passes through a bore 385 defined through the distal knob portion 384. A spring 386 rests on a shoulder 388 defined in the distal knob portion 384 about the bore 385. The spring 386 acts between the shoulder 388 and the flange 362.

The spring 386, along with the projections 364, 376, form a clutch mechanism. This clutch mechanism can be configured to slip when undesired pressures are reached in the delivery device 104. During use, when a user is rotating the knob 371, the projections 376 formed on the proximal knob portion 372 engage the projections 364 formed on the flange 362 of the plunger shaft 360. In particular, the angled surfaces 368, 380 engage one another as the user rotates the knob 371 clockwise. The spring 386 acts to keep the angled surfaces 368, 380 in engagement during normal operation. However, when undesired pressures are reached the angled surfaces 368, 380 begin to slip and the flange 362 separates from the proximal knob portion 372. As a result, the projections 364, 376 slide out of engagement thereby preventing further advancement of the plunger shaft 360 until pressure is normalized. Different spring constants can be used to alter the pressure at which the clutch mechanism is actuated. Furthermore, the projections 364, 376 could be oriented radially, as opposed to axially, such that axial forces supplied by the user does not affect the clutch mechanism's operation.

Figure 46:
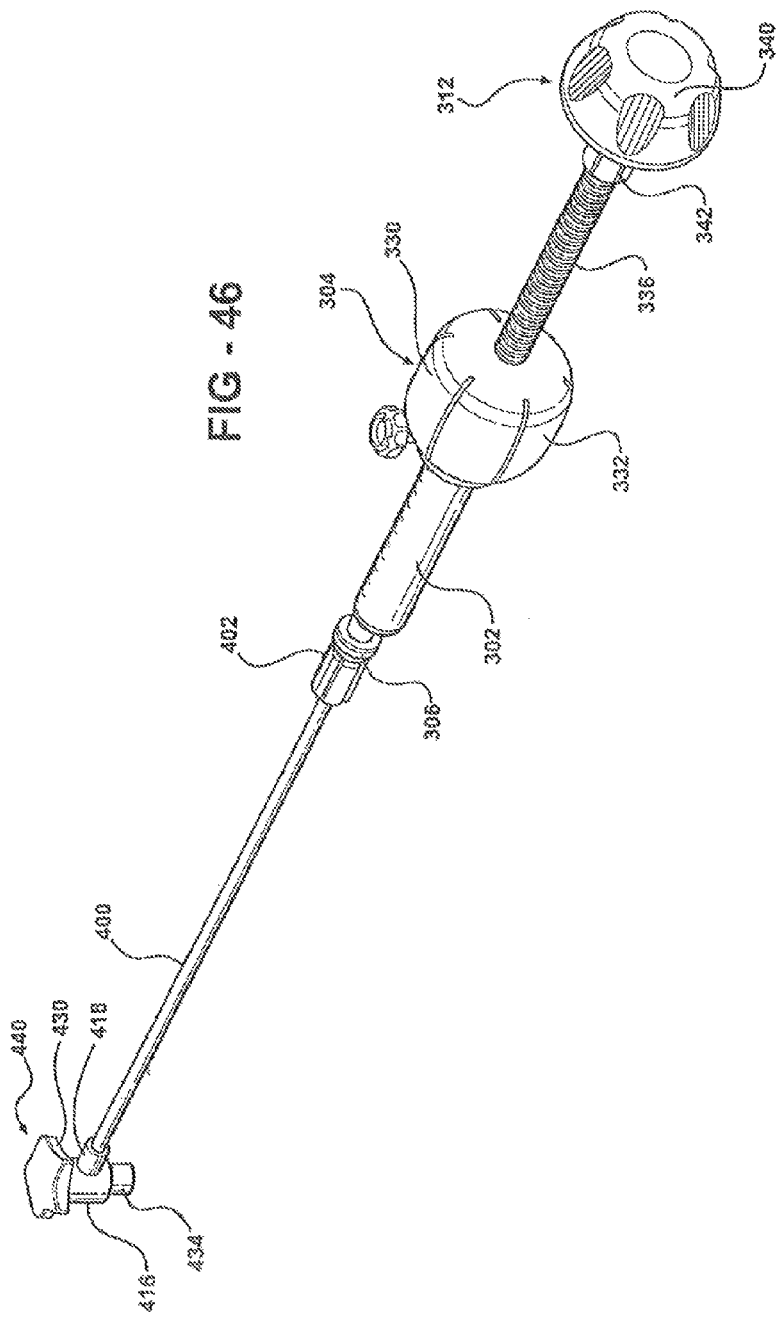
FIG. 46 is a top perspective view of the delivery device coupled to an extension tube and an enlarged luer-lock connector.
Figure 49:
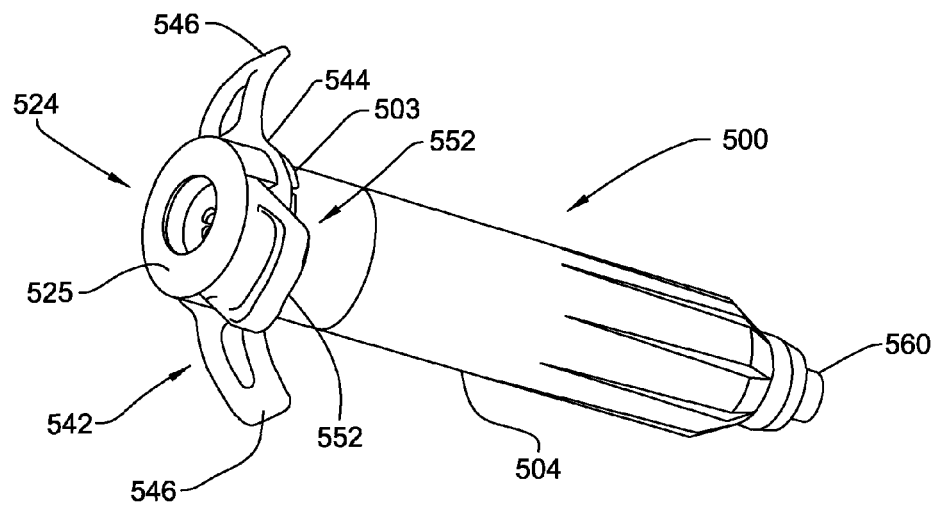
FIG. 49 is a perspective view of a monomer handling unit.
Figure 50:
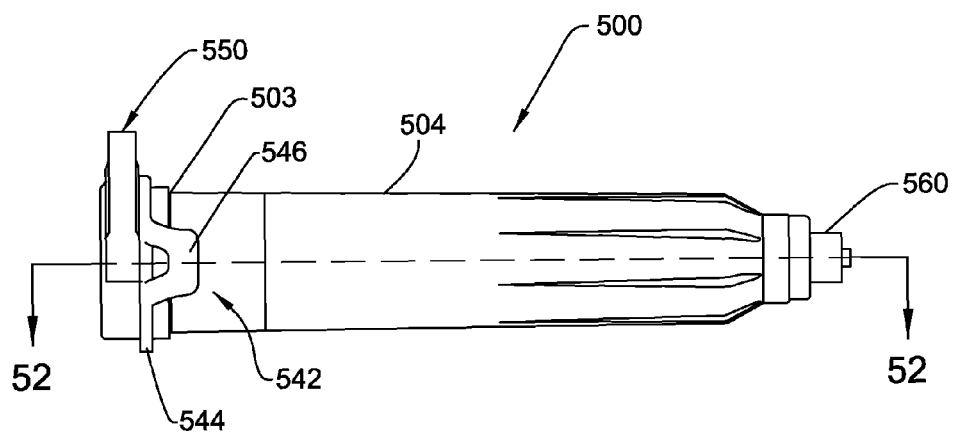
FIG. 50 is a side elevational view of the monomer handling unit.

Referring to FIG. 46, an extension tube 400 is shown mounted to the distal end of the reservoir 302. In one embodiment, the extension tube 400 is automatically primed with bone cement during the transfer phase. In other words, the system 100 is designed for use with specified bone cement mixture volumes that fill both the reservoir 302 and the extension tube 400 in the transfer phase. This eliminates the need for the user to prime the extension tube 400 manually.

Figures 47, 48:
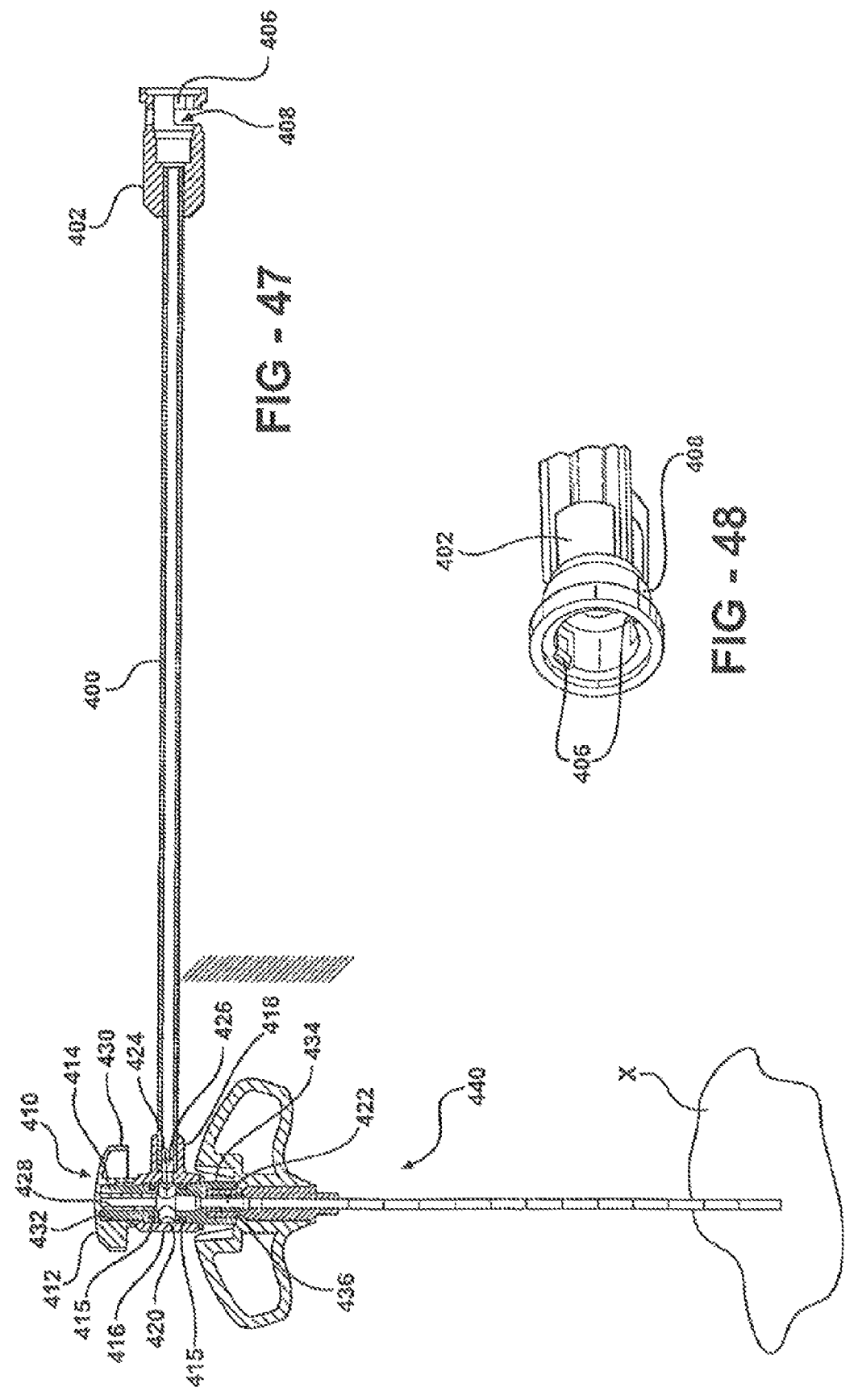

Referring to FIGS. 47-48, the extension tube 400 includes a tube fitting 402 for locking to the delivery port 306 of the reservoir 302. Referring back to FIG. 39, the delivery port 306 includes a pair of diametrically opposed projections 404 and the tube fitting 402 includes a pair of diametrically opposed channels 406 for receiving the projections 404 when the tube fitting 402 is axially mounted onto the discharge port 306. Once the projections 404 bottom-out in the channels 406, the tube fitting 402 is rotated. The projections 404 then ride in diametrically opposed slots 408 defined through the tube fitting 402. The tube fitting 402 is then prevented from axially sliding off the delivery port 306.

Referring to FIG. 47, an enlarged luer-lock connector 410 is mounted to a distal end of the extension tube 400. The luer-lock connector 410 comprises a knob 412, a spindle 414, and a collar 416. The collar 416 includes a side port 418 defining a side bore 426. A main bore 420 is defined through the collar 416 normal to the side port 418. The distal end of the extension tube 400 fits into the side bore 426 of the side port 418. The extension tube 400 may be fixed in the side port 418 by press fit, ultrasonic welding, adhesive, or the like.

The spindle 414 is rotatably supported in the main bore 420. A pair of o-rings 415 seals the spindle 414 in the main bore 420. The spindle 414 includes a throughbore 422 and a cross bore 424 aligned with the side bore 426 in the side port 418. The cross bore 424 is disposed between the o-rings 415. The knob 412 includes a stem 428 that fits into the throughbore 422 in a top of the spindle 414. The stem 428 is fixed in the throughbore 422 by a press-fit, ultrasonic welding, adhesive, or the like.

The knob 412 further includes a grasping portion 430 shaped for grasping by a hand of the user. The spindle 414 fits inside an annular cavity 432 in the knob 412. A bottom of the spindle 414 has a standard luer-lock fitting 434. The luer-lock fitting 434 is configured for attaching to a corresponding luer-lock fitting 436 on a delivery cannula 440. During use, the user grasps the grasping portion 430 of the knob 412 and rotates the knob 412 and spindle 414 to lock the luer-lock fitting 434 of the spindle 414 on the luer-lock fitting 436 on the delivery cannula 440. The oversized grasping portion 430 facilitates easier connection of the extension tube 400 to the delivery cannula 440 to deliver the bone cement mixture through the extension tube 400, the throughbore 422, the delivery cannula 440, and to the target site X.

The reservoir 302, rotatable fitting 322, handle 304, knob 312, plunger 310, nut 324, valve housing 316, tube fitting 402, and enlarged luer-lock connector 410 are preferably formed of a bio-compatible plastic material such as nylon, PBT (polybutylene terephthalate), PC (polycarbonate), ABS (acrylonitrile butadiene styrene), glass-filled nylon, glass-filled polyetherimide, or the like. The umbrella valve 320 is preferably formed of nitrile.

III. Monomer Handling Unit

Referring to FIGS. 49-52, the monomer handling unit is generally shown at 500. The monomer handling unit 500 stores an ampoule of monomer and releases the monomer from the ampoule when desired. In one embodiment, described herein, the monomer handling unit 500 stores a glass ampoule 502 of liquid monomer and releases the liquid monomer from the ampoule to combine, under suitable conditions, with an appropriate amount of a powder component of bone cement or other material to form a desired bone cement mixture medical use.

Referring specifically to FIGS. 51-55, the monomer handling unit 500 comprises a cartridge 504 having proximal and distal ends. A lid 503 having an opening defined therethrough is fixed to the proximal end of the cartridge 504. The lid 503 is ring-shaped and includes a plurality of flexible clipping portions 505 for snap-fitting onto a rim 507 at the proximal end of the cartridge 504. This prevents removal of lid 503 once assembled on to cartridge 504. In some embodiments, lid 503 is further, or instead, secured to the cartridge 504 by an adhesive.

Referring to FIGS. 51-52 and 56-60, a plunger 510 is slidably disposed in the cartridge 504 through the opening of the lid 503. The plunger 510 includes a retainer 512 for securing the glass ampoule 502 to the plunger 510. In the preferred embodiment, the retainer 512 includes a plurality of flexible legs 514 extending downwardly from a head 516 of the plunger 510. In the embodiment shown, two flexible legs 514 are utilized. These flexible legs 514 are diametrically opposed from one another relative to a center of the retainer 512. In other embodiments, additional flexible legs 514 can be used.

Each of the flexible legs 514 includes a protruding portion 518 defining a pocket 520 for receiving the glass ampoule 502. The pockets 520 have a shape complimentary to a neck 522 of the glass ampoule 502. Each of the flexible legs 514 flex outwardly as the glass ampoule 502 is inserted into the retainer 512 until the glass ampoule 502 is inserted far enough that the protruding portions 518 reach the neck 522 and spring back into position around the neck 522. The flexible legs 514 are normally biased to this position. The flexible legs 514 are designed such that they flex radially outward to receive the glass ampoule 502, but are rigid when pushed axially so as to advance the glass ampoule 502 distally in the cartridge 504. In other embodiments of the monomer handling unit 500, the plunger 510 does not include the legs 514. That is, the ampoule 502 is free-standing within the cartridge 504. In such embodiments, the relative dimensioning of the ampoule 502 and cartridge is such that the side-to-side movement of the ampoule is limited. In some of these versions of the invention, an alignment member is disposed within the cartridge 504 to properly align the ampoule 502 within the cartridge 504

In the embodiment shown, the ampoule 502 is made entirely of glass to prevent reaction between the monomer and the ampoule 502. A reaction between the monomer and a non-glass ampoule could result in deterioration of the ampoule, which in turn could result in premature release of monomer.

Ampoule 502 is preferably amber-colored. The amber coloring is intended to prevent degradation of the monomer. The ampoule 502 can also be clear, partially opaque, or completely opaque, depending on the monomer contained within the ampoule 502.

Referring to FIGS. 51-52 and 61-63, a push cap 524 is fixed to the head 516 of the plunger 510. The cap 524 and plunger 510 can also be made of a single integral piece. The two-piece construction allows for easy placement of the lid 503 around the cap 524 and plunger 510 during construction.

The head 516 defines an outer annular groove 526 for receiving a dynamic seal 528 to seal the head 516 along an inner surface of the cartridge 504 as the head 516 slides along the inner surface. A user presses the push cap 524 to slide the plunger 510 and the glass ampoule 502 distally in the cartridge 504. The top portion 561 of the annular groove 526 forms a lip. Upon movement of the plunger 510 in a proximate direction, the top portion 561 of the annular groove 526 abuts a bottom surface of the lid 503, preventing removal of the plunger 510 and the ampoule 502 from the cartridge 504. Thus, once the ampoule 502 is placed in the cartridge 504, and the cap 524 and plunger 510 fitted over the proximate end of the cartridge 504, the ampoule 502 is effectively sealed within the cartridge 504. This substantially reduces the likelihood that curious fingers can gain access to the ampoule 502 in either its whole or shattered states.

The push cap 524 includes a top portion 525 and an annular-shaped wall 527 extending distally from the top portion 525. A plurality of tabs 529 having locking projections 531 are disposed on the top portion 525 at its outer periphery. The tabs 529 extend distally in a cantilevered fashion. The tabs 529 are flexible and are spaced radially from the annular-shaped wall 527 to define an annular pocket 533. The tabs 529 are also circumferentially spaced from one another to define entry paths 535 with access to the annular pocket 533.

Figure 64:
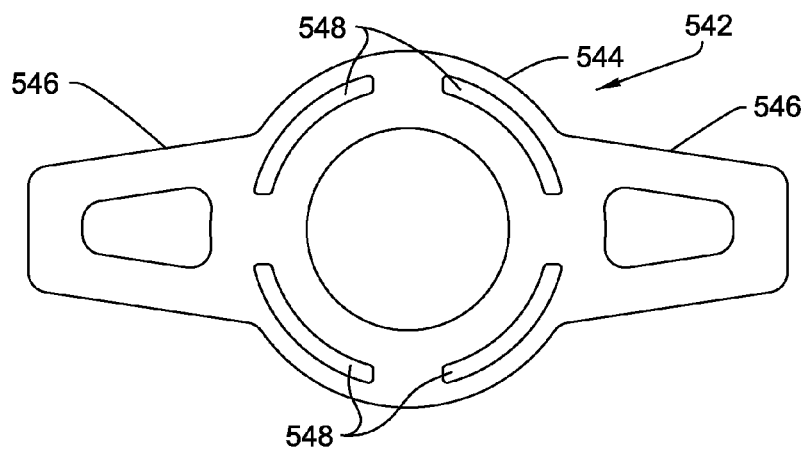
FIG. 64 is a top view of a handle of the monomer handling unit.

Referring to FIGS. 51-52 and 61-64, a handle 542 locks to the push cap 524 once the push cap 524 and plunger 510 have been moved a predetermined distance in the cartridge 504. As shown in FIG. 64, the handle 542 includes a ring-shaped hub 544. A pair of grips 546, diametrically opposed to one another, extends outwardly from the hub 544. The grips 546 extend radially outwardly from the hub 544. The hub 544 includes a plurality of arc-shaped slots 548 circumferentially spaced about the hub 544.

The arc-shaped slots 548 are sized and shaped to receive the tabs 529 of the push cap 524. Initially, prior to use, the tabs 529 are only partially started in the arc-shaped slots 548. However, as the user presses the push cap 524, the tabs 529 are further inserted into the handle 542 until the locking projections 531 pass through the arc-shaped slots 548. The tabs 529 flex radially inwardly as the locking projections 531 (formed as ramps) pass through the arc-shaped slots 548. Once through the arc-shaped slots 548, the locking projections 531 return to their normally biased position and prevent the push cap 524 from being removed from the handle 542.

Referring to FIGS. 51-52 and 65-67, a shattering assembly 530 is disposed inside the cartridge 504 near the distal end to shatter the glass ampoule 502. Shattering occurs when the glass ampoule 502 reaches the shattering assembly 530 as the user presses the push cap 524. This breaks, shatters the glass ampoule 502 to release the liquid monomer. The flexible legs 514 are configured such that the glass ampoule 502 is advanced with sufficient force into the shattering assembly 530 to break the glass ampoule 502.

Figure 65:
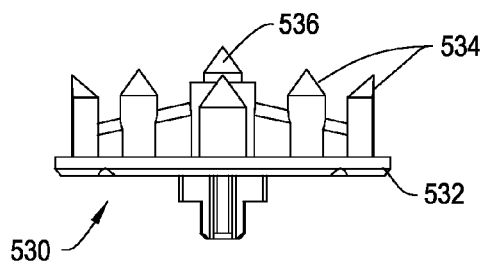
FIG. 65 is a side elevational view of a shattering assembly and screen of the monomer handling unit.
Figure 66:
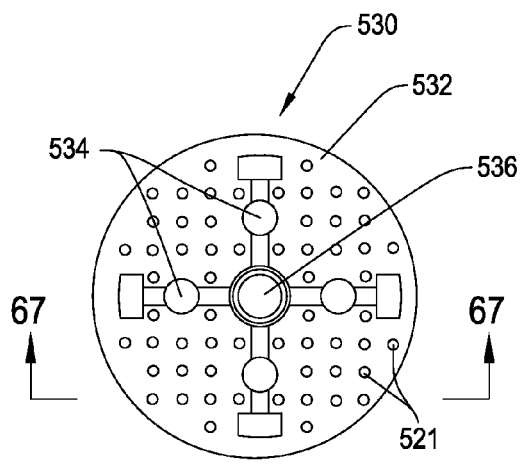
FIG. 66 is a top view of the shattering assembly and screen.
Figure 67:
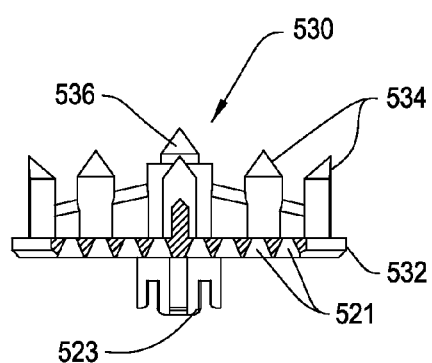
FIG. 67 is a cross-sectional view of the shattering assembly and screen taken generally along the line 67-67 in FIG. 66.

As shown in FIGS. 65-67, the shattering assembly 530 comprises a cylindrical plate 532 having a plurality of spikes 534 extending upwardly from the plate 532. A central spike 536 extends past the remaining spikes 534 such that the central spike 536 strikes a bottom of the glass ampoule 502 first to initially crack the glass ampoule 502, while the remaining spikes 534 further shatter the glass ampoule 502 as it continues distally. Some of the spikes 534 may be shorter than other spikes 534. When the glass ampoule 502 is shattered, the liquid monomer passes through a plurality of holes 521 defined through the plate 532. Shattering the bottom of the ampoule 502 ensures that substantially all of the entire contents of the ampoule 502 are released from the ampoule 502. In this manner, the plate 532 acts as a screen to strain glass pieces from the liquid monomer. Some other versions of the monomer handling unit 500 need not include a screen or can have the screen positioned elsewhere along the path that the monomer takes during the ejection process. In still other versions of the monomer handling unit 500, in which the monomer handling unit 500 is connected to a cement mixer, the screen can be part of the cement mixer and not part of the monomer handling unit 500. It should be understood that any number of spikes 534, 536 can be employed, including a single central spike 536. It should further be understood that the spikes 534 can have multiple heights and/or be the same height as central spike 536.

Figure 51:
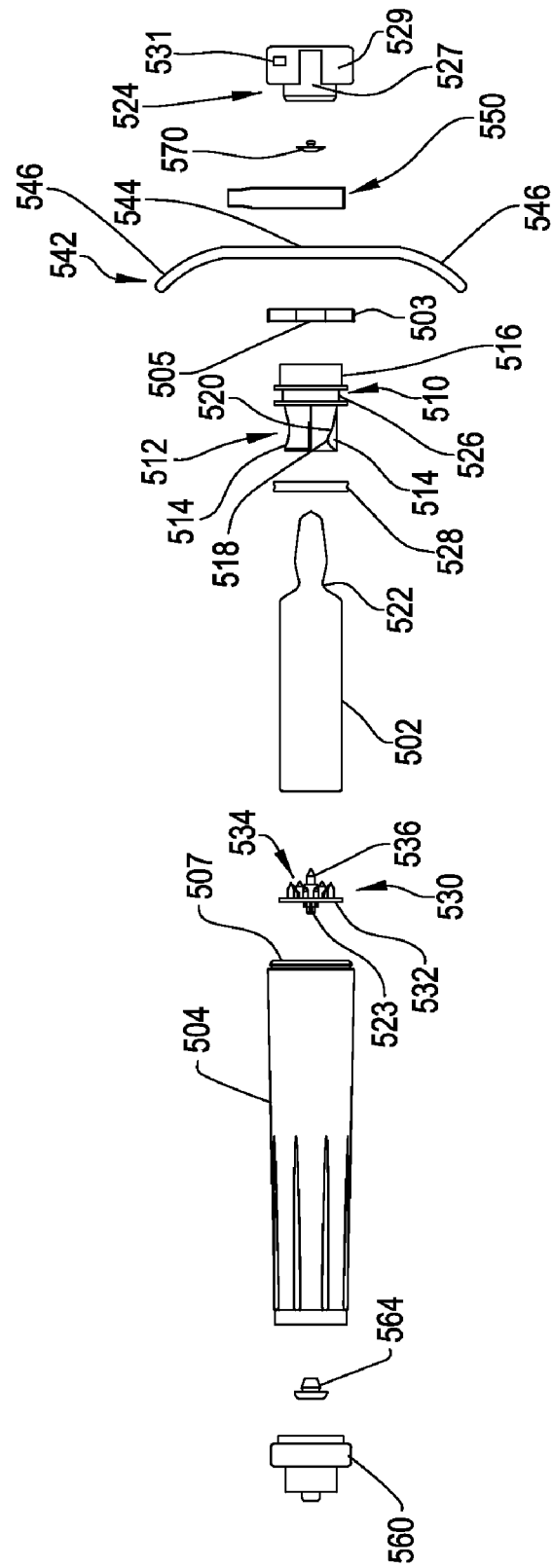
FIG. 51 is an exploded elevational view of the monomer handling unit.
Figure 56:
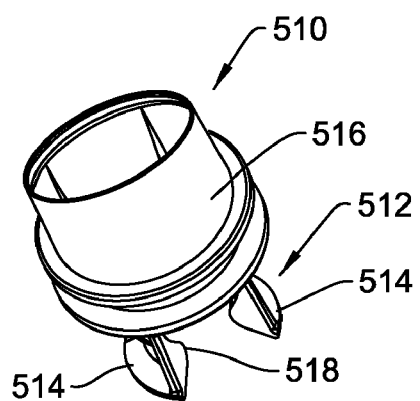
FIG. 56 is a top perspective view of a retainer of the monomer handling unit.
Figure 57:
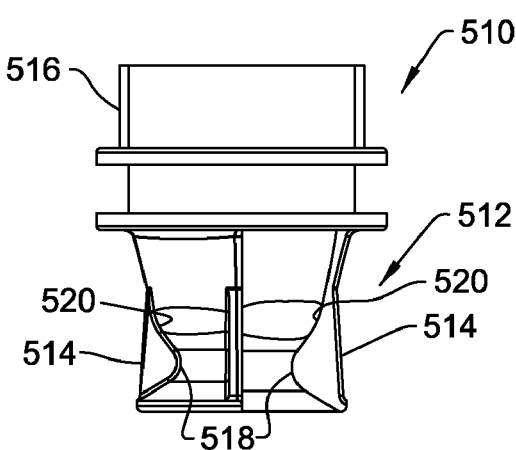
FIG. 57 is a side elevational view of the retainer.
Figure 59:
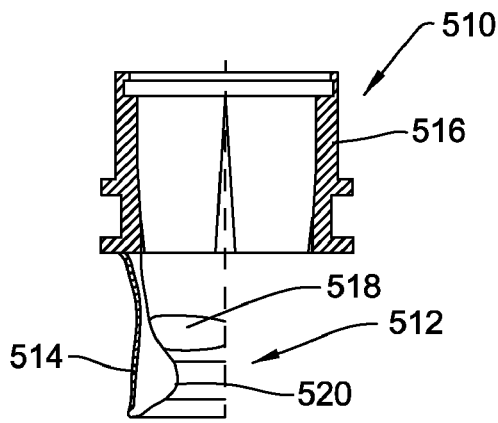
FIG. 59 is a cross-sectional view of the retainer taken generally along the line 59-59 in FIG. 58.
Figure 60:
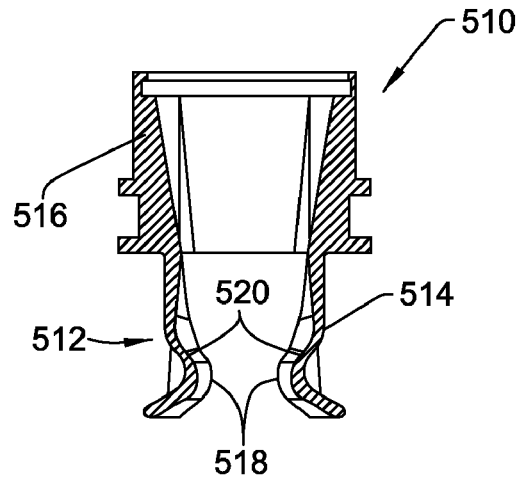
FIG. 60 is a cross-sectional view of the retainer taken generally along the line 60-60 in FIG. 58.
Figure 58:
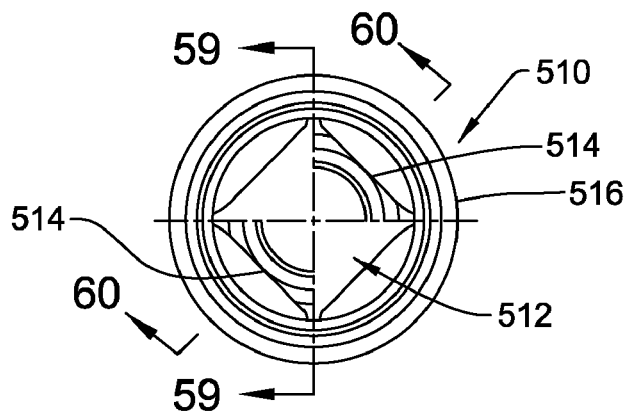
FIG. 58 is a top view of the retainer.
Figure 61:
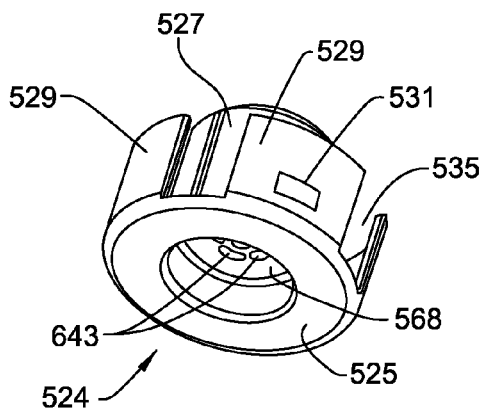
FIG. 61 is a top perspective view of a push cap of the monomer handling unit.
Figure 62:
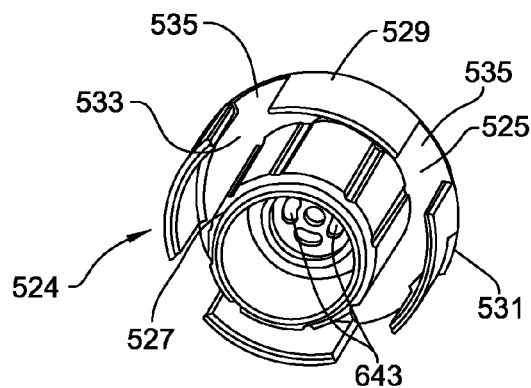
FIG. 62 is a bottom perspective view of the push cap.
Figure 63:
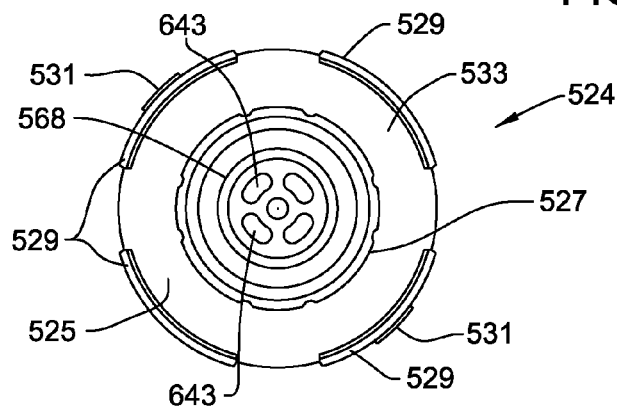
FIG. 63 is a bottom view of the push cap.
Figure 68:
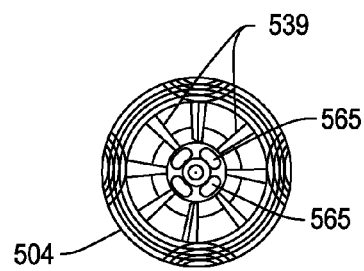
FIG. 68 is a top view of a cartridge of the monomer handling unit.

Referring to FIGS. 51-52 and 68, the plate 532 is supported on a plurality of structural support webs 539 disposed in the distal end of the cartridge 504. These webs 539 are preferably integrally formed with the cartridge 504. Referring specifically to FIG. 68, the webs 539 are circumferentially spaced along the inner surface of the cartridge 504 and extend radially inwardly from the inner surface toward a center of the cartridge 504. A distally facing hub 523 on the plate 532 is secured centrally at the ends of the webs 539 in the center of the cartridge 504 to hold the plate 532 in place. In other embodiments, the cartridge 504 includes two or more inwardly projecting tabs (not shown) on the inside surface of the cartridge 504. The tabs are preferably formed integrally with the cartridge 504. The tabs are positioned proximal to the webs 539 and secure the plate 532 in place between the tabs and the webs 539.

Figure 69:
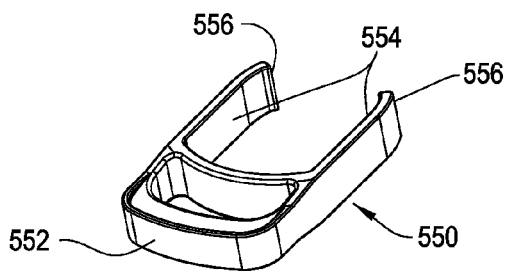
FIG. 69 is a perspective view of a release clip of the monomer handling unit.

Referring to FIGS. 51-52 and 69, during assembly, a release clip 550 is initially inserted through the entry paths 535 into the annular pocket 533 to prevent the user from pressing the push cap 524 distally to unintentionally break the glass ampoule 502. This minimizes the likelihood of inadvertent release of the liquid monomer from the monomer handling unit 500. The release clip 550 includes a grasping portion 552 and a pair of fingers 554 that extend away from the grasping portion 552. The fingers 554 pass through two of the entry paths 535 of the push cap 524 into the annular pocket 533. The fingers 554 rest between the top portion 525 of the push cap 524 and the hub 544 of the handle 542. The fingers 554 further include bent ends 556 that are bent toward one another. The bent ends 556 flex outwardly on opposing sides of the annular-shaped wall 527 when being inserted into the annular pocket 533. Once past the annular-shaped wall 527, the bent ends 556 return to their normally biased position and help to prevent inadvertent removal of the release clip 550. Once the release clip 550 is removed, the push cap 524 is pressed distally by pressing the user's finger or hand against the push cap 524 or by striking the push cap 524 against a surface.

Referring to FIG. 52, a luer-lock connector 560 is fixed to the distal end of the cartridge 504 by adhesive, press-fit and the like. The distal end of the cartridge 504 further includes a valve seat 562 for receiving a umbrella valve 564. The umbrella valve 564 is normally in a closed position to hold the monomer in the cartridge 504 until such time as its release is required. The cap 524 also includes a valve seat 568 for receiving an umbrella valve 570. The umbrella valve 570 is also normally in a closed position. The valve seat 568 defines a plurality of openings 643 (see FIG. 63). Both umbrella valves 564 and 570 each open in response to a pressure differential between the ambient air pressure and the pressure within the cartridge 504.

Such a construction results in a self-contained monomer storage unit in which the monomer can be stored until it is desired that it be released. The monomer handling unit 500 also minimizes the release of any gases from the monomer and into the ambient environment. Moreover, the user can break the ampoule 502 without releasing the monomer, or any gases, contained within the ampoule 502 until desired, allowing greater user control and flexibility.

In operation, the user first removes the release clip 550. Once removed, the user then presses the push cap 524 to urge the plunger 510 and glass ampoule 502 distally in the cartridge 504 until a bottom of the glass ampoule is shattered first by the central spike 536 and then by the remaining spikes 534. At this point, the monomer is released and flows through the screen, e.g., through holes 521 in the plate 532. At the same time, the push cap 524 locks to the handle 542. More specifically, the tabs 529 slide through the arc-shaped slots 548 until the locking projections 531 snap-fit in place past the arc-shaped slots 548. This forms the cap/handle assembly.

During this initial depression of the plunger 510, the plunger 510 travels a distance equal to that of release clip 550, approximately 0.75 cm. Owing to the relative short stroke of this depression, there is minimal increase of pressure inside the cartridge 540. Umbrella valve 564 is a pressure set valve that is set to open only when there is an appreciable difference in pressure inside the cartridge 504 in comparison to the ambient pressure. (Umbrella valve 564 opens in response to a relatively large cracking pressure.) The pressure build up in this initial depression of the plunger 510 is not sufficient to overcome the forces holding the umbrella valve 564 closed. Thus, at this stage of the monomer discharge process, even though the monomer is in a pool in the bottom of the cartridge 504, the umbrella valve 564 prevents release of the monomer. Thus, the umbrella valve 564 holds the monomer in the cartridge 504 after shattering the ampoule 502 but prior to subsequent discharge of the monomer.

It should likewise be appreciated that the cracking pressure of umbrella valve 564 should also be high enough to prevent it from opening from the weight of the monomer pooled above the umbrella valve 564.

When discharge of the monomer is required, the cap/handle assembly is retracted (i.e., pulled proximally away from the distal end of the cartridge 504). Sometimes, after shattering, the top of the ampoule 502 remains intact. In this situation, an air pocket can develop in the remaining intact portion of the ampoule. The presence of this air pocket can impede the subsequent discharge of monomer. However, when the plunger 510 is retracted, plunger legs 514 pull the unshattered portion of the ampoule 502 away from the pool of monomer at the bottom of the cartridge 504. This motion breaks the air pocket that may have formed in the unshattered portion of the cartridge 504.

Further, as a result of the retraction of the plunger 510, the volume of the void space internal to the cartridge 504 increases. There is, however, no change in the contents in this space. Accordingly, the pressure inside the cartridge 504 drops and more particularly to a pressure below that of the ambient air. Umbrella valve 570 is set to open when there is a relatively small difference in pressure between the environment and within the cartridge 504. In other words, umbrella valve 570 opens in response to the application of a relatively small cracking pressure. The opening of umbrella valve 570 allows air to flow into the cartridge 504 to equalize the cartridge internal pressure to the atmospheric pressure.

The cap/handle assembly is then again pushed towards the distal end of the cartridge 504 to force the liquid monomer out of the cartridge 504. The liquid monomer passes through the screen. During this step, plunger 501 is urged a greater distance distally than in the first, ampoule-shattering depression of the plunger 510. In some versions of this invention, this distance is approximately 2.90 cm. As a consequence, the gas in the cartridge 504 is subjected to greater compression than the gas present during the initial depression. The pressure difference between the inside of the plunger 510 and the ambient atmosphere is therefore greater than the difference during the first depression of the piston. This pressure difference is enough to overcome the force closing the umbrella valve 564. The umbrella valve 564 opens to thereby allow discharge of the monomer.

The luer-lock connector 560 is initially locked to the luer-lock fitting 246 of the cement mixer 102 (see FIG. 32) before releasing the liquid monomer from the glass ampoule 502. This way the user's exposure to the liquid monomer is significantly reduced.

The cartridge 504, plunger 510, lid 503, push cap 524, release clip 550, handle 542, shattering assembly 530, and luer-lock connector 560 are preferably formed of a bio-compatible plastic material such as nylon, PBT (polybutylene terephthalate), PC (polycarbonate), ABS (acrylonitrile butadiene styrene), glass-filled nylon, glass-filled polyetherimide, or the like. The umbrella valves 564, 570 are preferably formed of silicone. The central spike 536 is preferably made of metal. The remaining spikes 534 are preferably formed integrally with the plate 532 and made of the same material as plate 532.

Figure 70:
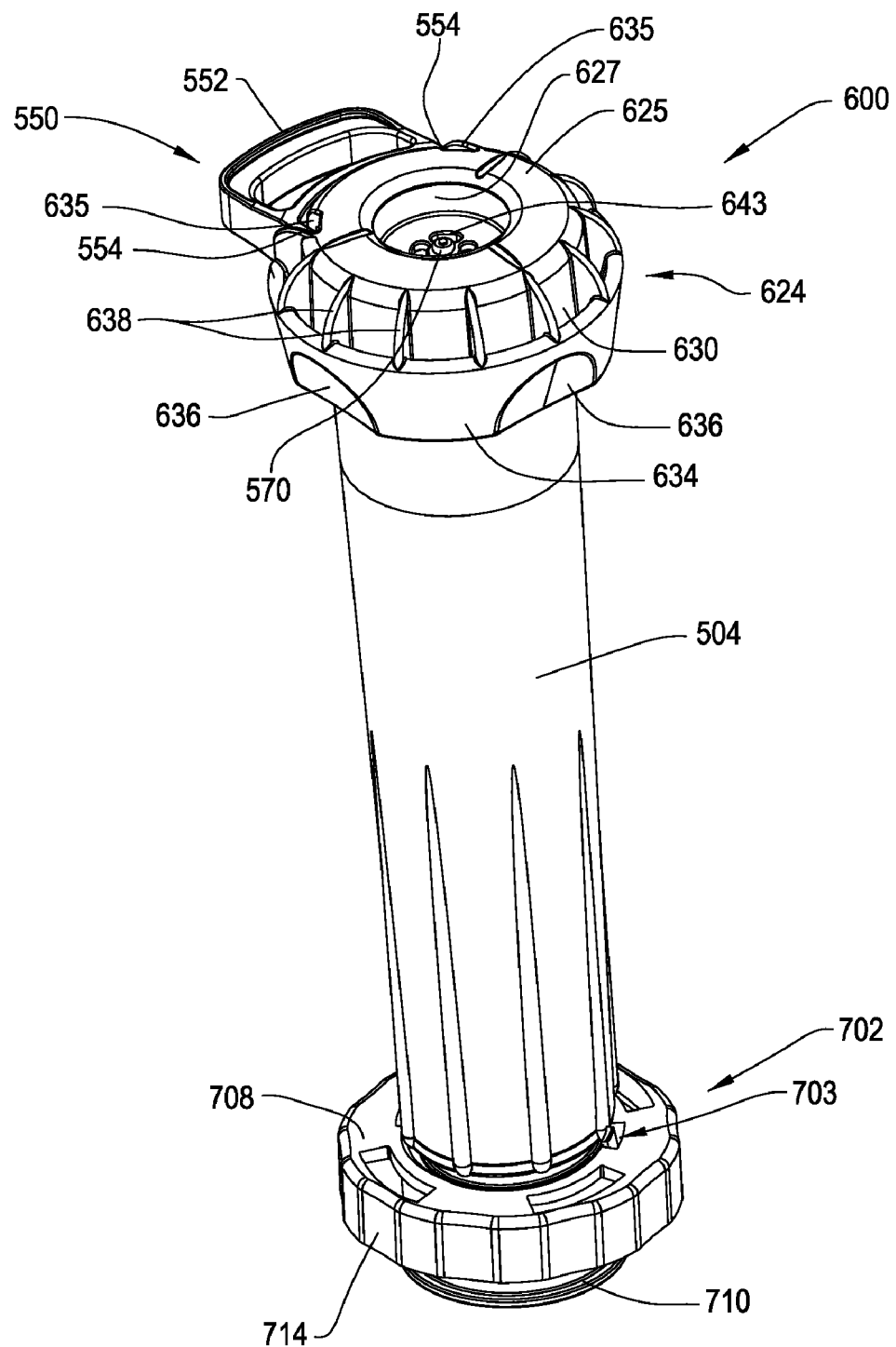
FIG. 70 is a perspective view of an alternative monomer handling unit.
Figure 71:
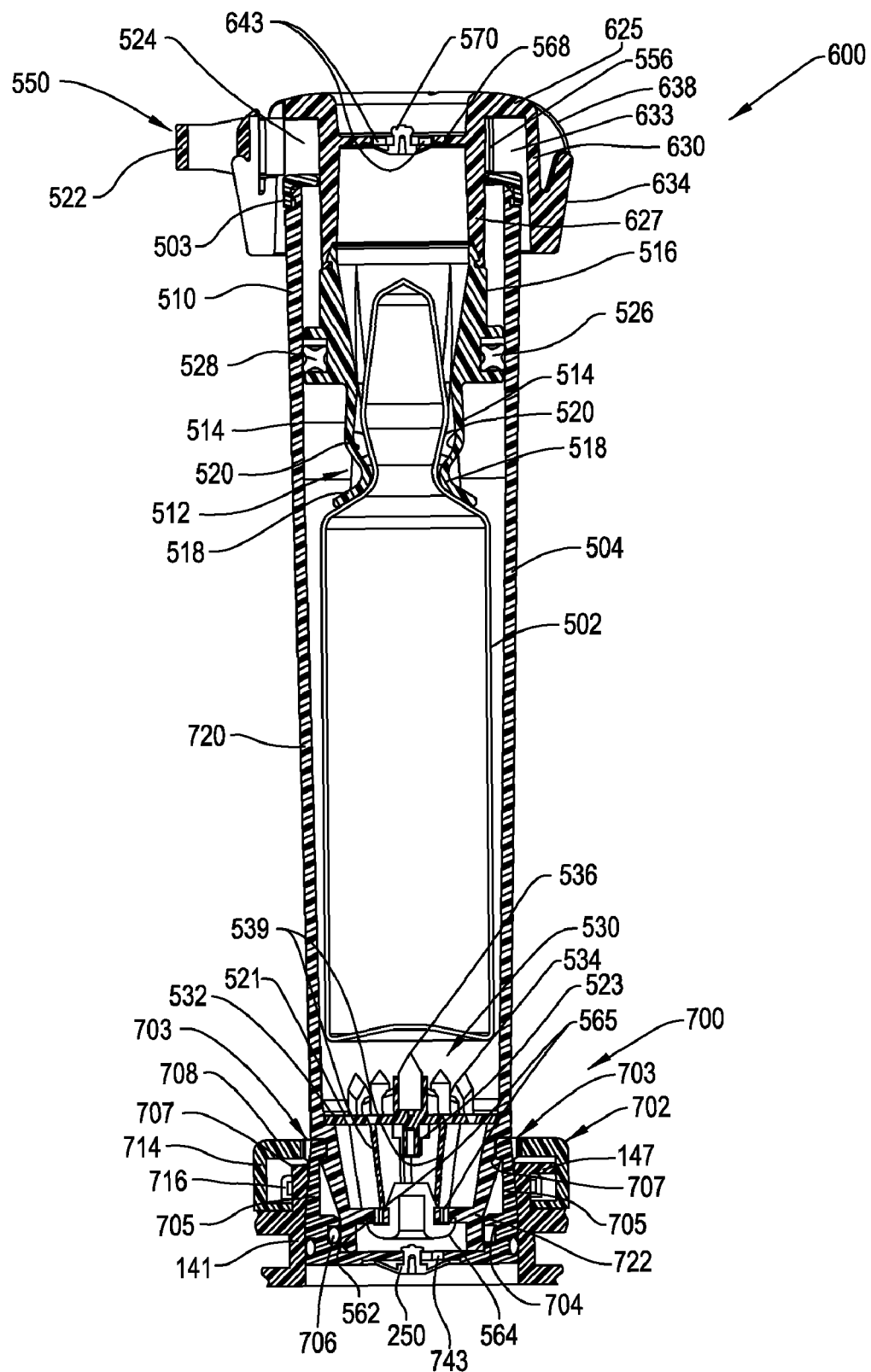
FIG. 71 is a cross-sectional view of the alternative monomer handling unit of FIG. 70.

Referring to FIGS. 70 and 71, an alternative monomer handling unit is generally shown at 600. The alternative monomer handling unit 600 is similar to the monomer handling unit 500 described above, except that the push cap 624 has a different configuration than the prior push cap 524 such that the separate handle 542 is not required. For convenience, the same numerals indicate like or corresponding parts between the units 500, 600.

The push cap 624 is fixed to the head 516 of the plunger 510. The push cap 624 includes a top portion 625 and an annular-shaped inner wall 627 extending distally from the top portion 625. An outer annular wall 630 also extends downwardly from the top portion 625. The outer annular wall 630 is radially spaced outwardly from the inner annular wall 627 to define an annular pocket 633. A pair of entry paths 635 are defined through the outer annular wall 630 to provide access to the annular pocket 633. A gripping flange 634 extends from the outer annular wall 630. The gripping flange 634 includes a plurality of thumb/finger gripping portions 636 for a grasping by a user to pull the push cap 624 as described further below. A plurality of support ribs 638 extend between the outer annular wall 630 and the gripping flange 634 to reinforce the gripping flange 634.

In this embodiment, during assembly, the release clip 550 when in an engaged state extends through the entry paths 635 into the annular pocket 633 to block the user from pressing the push cap 624 distally to break the glass ampoule 502. This prevents inadvertent release of the liquid monomer from the monomer handling unit 600. The release clip 550 includes a grasping portion 552 and a pair of fingers 554 that extend away from the grasping portion 552. The fingers 554 pass through the two entry paths 635 of the push cap 624 into the annular pocket 633. The fingers 554 rest between the top portion 625 of the push cap 624 and the lid 503. When the release clip 550 is removed, disengaged from the cartridge and plunger, the push cap 624 can be pressed distally (by pressing of the user's finger or hand against the push cap 624 or by striking the push cap 624 against a surface).

Figure 72:
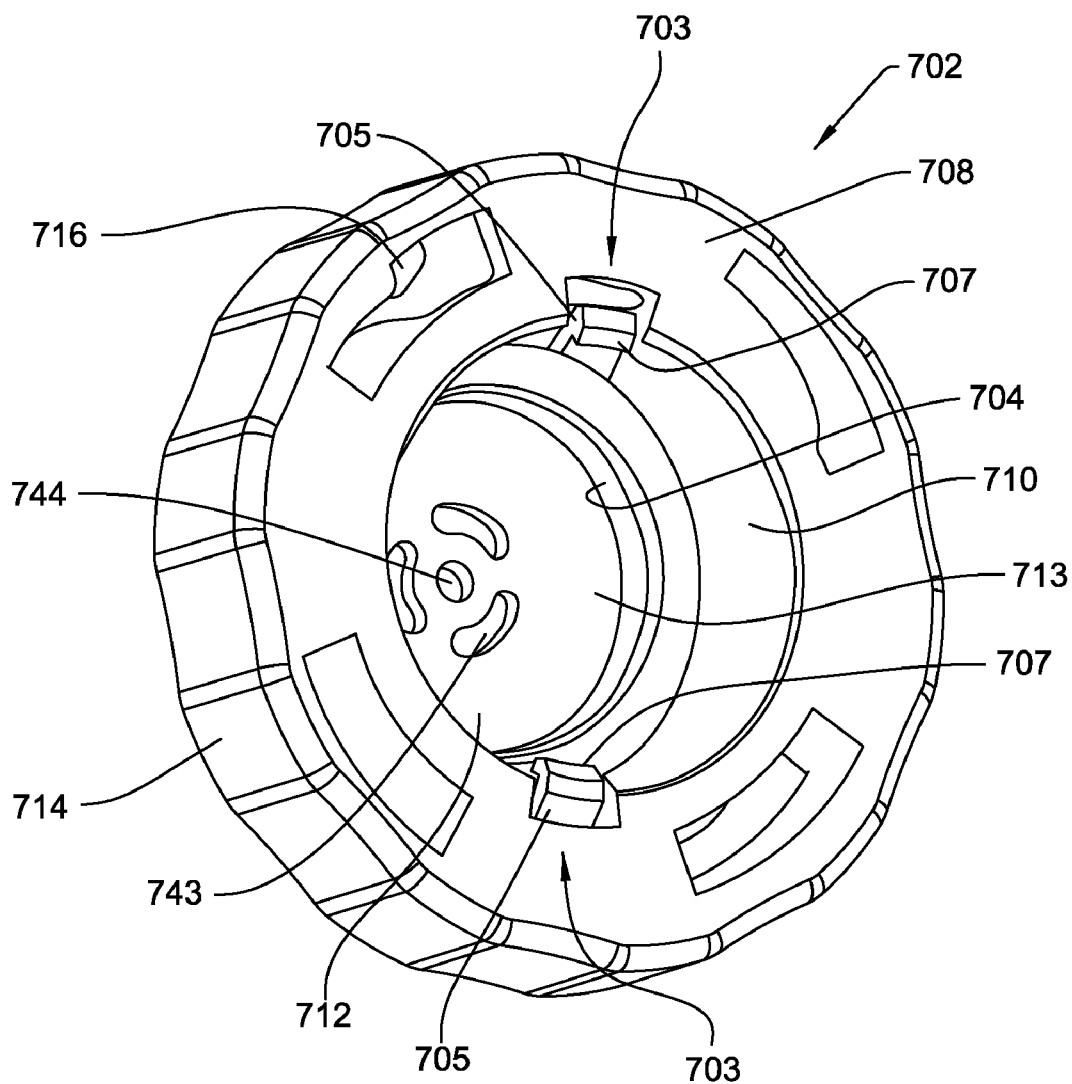
FIG. 72 is a top perspective view of another alternative cap of the mixer for use with locking the alternative monomer handling unit of FIG. 70 to the mixer.
Figure 73:
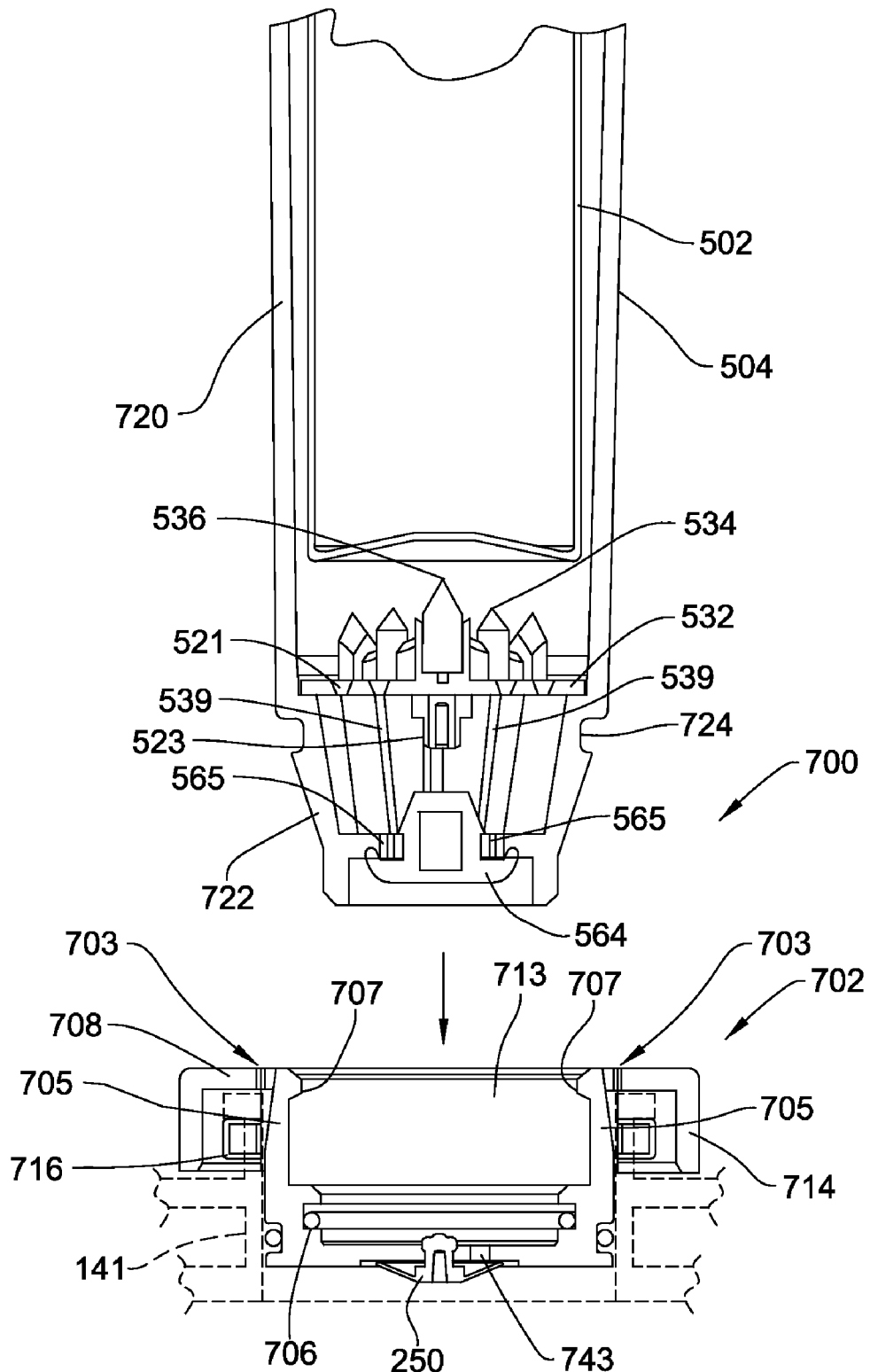
FIG. 73 is a cross-sectional view illustrating a distal end of the alternative monomer handling unit of FIG. 70 just prior to engagement with the alternative cap of FIG. 72.

Referring to FIGS. 71-73, the luer-lock fittings or connectors 246, 560 can be replaced by the engagement mechanism 700 shown to attach the alternative monomer handling unit 600 to the mixer 102. Alternatively, the luer-lock fittings or connectors 246, 560 could be used to attach the alternative monomer handling unit 600 to other mixers, etc.

In FIGS. 72 and 73, an alternative cap 702 is used with the mixer 102. In this embodiment, the cap 702 is shaped similarly to the prior disclosed caps 140, 230, but further includes the snap-locking tabs 703 and an inner annular groove 704 for receiving an o-ring 706 (see FIG. 73). The cap 702 includes a top 708. A cap wall 710 is disposed on the top 708 and extends downwardly from the top 708 to a bottom wall 712. A central opening 744 and surrounding flow paths 743 are defined in the bottom wall 712. The cap wall 710 and bottom wall 712 also define a pocket 713 leading to the flow paths 743. The snap-locking tabs 703 include arms 705 with a lip 707 extending from each of the arms 705. A gripping flange 714 extends downwardly from the top 708 and is spaced from the cap wall 710. A plurality of locking tabs 716 are disposed on the gripping flange 714 and extend radially inwardly into a gap between the gripping flange 714 and the cap wall 710. The locking tabs 716 engage the tabs 147 on the top port 141.

Referring to FIG. 73, with the cap 702 secured to the top port 141 of the mixer housing 108, the alternative monomer handling unit 600 can be locked to the cap 740 by inserting a distal end of the cartridge 504 of the alternative monomer handling unit 600 into the pocket 713. In this embodiment, the cartridge 504 includes a cylindrically-shaped outer wall portion 720. A conically-shaped outer wall portion 722 extends downwardly from the cylindrically-shaped outer wall portion 720 at the distal end of the cartridge 504. A groove 724 is defined between the wall portions 720, 722 to receive the lips 707 of the snap-locking tabs 703.

When the distal end of the cartridge 504 is pressed into the pocket 713, the arms 705 of the snap-locking tabs 703 flex radially outwardly from their normally biased position until the groove 724 is aligned with the lips 707. At that point, the arms 705 snap back into their normally biased position with the lips 707 resting in the groove 724 to prevent release of the cartridge 504 from the cap 702. The o-ring 706 seals to the cartridge 504 to prevent the release of odors from the mixing chamber 138 and around the cartridge 504 and to prevent the liquid monomer from leaking outside the cartridge 504.

In operation, the user first removes the release clip 550. Once removed, the user then presses the push cap 624 to urge the plunger 510 and glass ampoule 502 distally in the cartridge 504 until a bottom of the glass ampoule is penetrated first by the central spike 536 and then by the remaining spikes 534. At this point, the liquid monomer is released and flows through the screen, e.g., through holes 521 in the plate 532.

At this point, the push cap 624 can be retracted (i.e., pulled proximally away from the distal end of the cartridge 504) to force any remaining liquid monomer in the glass ampoule 502 into the cartridge 504 and to allow air into the cartridge 504 through the openings 643 (via the second umbrella valve 570 which opens/closes the openings 643). This maintains the pressure in the cartridge 504 at nearly atmospheric pressure. More specifically, the pressure in the cartridge 504 is at the cracking pressure of the second umbrella valve 570, which has been selected as being close to atmospheric pressure. By utilizing the second umbrella valve 570, a negative pressure is not pulled in the cartridge 504, when the push cap 624 is retracted. As a result, based on Boyle's Law, pressure can build in the cartridge 504 when the push cap 624 is again pushed.

The push cap 624 is pushed distally towards the distal end of the cartridge 504 to force the liquid monomer out of the cartridge 504. The liquid monomer passes through the screen, the umbrella valve 564 (via openings 565 in the valve seat 562 that open/close via the umbrella valve 564), through the umbrella valve 250 (via openings 743 in the cap 702 controlled by the umbrella valve 250) and into the mixer 102 where it can be combined with the powder component to form the bone cement mixture. At this point, the openings 643 are closed to atmosphere thereby allowing pressure to building inside the cartridge 504 to force the monomer out.

It should be appreciated that the monomer handling unit 500 of this invention is therefore designed to allow a monomer container to be broken open, so the monomer is readily available for use, without allowing immediately exposing the monomer to the ambient environment. The holding of the monomer in cartridge 504 thus prevents the release of fumes the exposed monomer would otherwise release. When the monomer handling unit 500 is coupled directly to a cement mixer, there is essentially no release of fumes. In addition, the sharp edges of the broken ampoule 502 and the broken pieces of glass are kept within a closed environment.

It should likewise be understood that this invention may have features different from what has been described. There is no reason, for example, that the valve 570 that is used to vent air into the cartridge 504 always be attached to the cap 524. In some versions of the invention, this valve 570 may be mounted directly to the cap 524. As another example, another type of a one-way valve, other than an umbrella valve, can be used.

It should be understood that the monomer handling units 500 and 600 need not be used with any specific type of mixer 102 or any specific type of cap 140, 702. Monomer handling units 500 and 600 can be used with the bone cement mixing and delivery system 100 described herein or with another type of enclosed cement mixer. Alternative coupling assemblies can be employed to couple the cartridge 504 to the complementary mixer. In addition, the embodiments of the monomer handling unit 500 and 600 can be used with an open cement mixer. It should be appreciated that even when handling unit 500 or 600 is used with this of type of mixer, the release of noxious vapors is at least reduced, because the pooled monomer remains enclosed in the cartridge 504 until the time it is injected directly into the mixer.

Likewise, while in one preferred version of the invention an assembly is provided that is specifically designed to shatter the ampoule 502 into small pieces, such an assembly may not always be required. In alternative versions of the invention, the ampoule 502 may be formed from material other than glass that may not need to be so shattered. Thus, other assemblies can be used to break, crack, the ampoule 502 open. For example, an assembly with a single pin or surface that cracks the ampoule 502 along a single break line is possible.

While this description is directed to a few particular embodiments, it is understood that those skilled in the art may conceive of modifications and/or variations to the specific embodiments shown and described herein. Any such modifications or variations that fall within the purview of this description are intended to be included herein as well. It is understood that the description herein is intended to be illustrative only and is not intended to be limited.

What is claimed is:

1. An apparatus for storing and discharging bone cement monomer, said apparatus comprising:
    a cartridge having opposed top and bottom ends and a void space between said ends;
    a coupling member located below the bottom end of said cartridge, said coupling member configured to attach said cartridge to a bone cement mixer and allow fluid to flow into the bone cement mixer;
    a cracking assembly mounted to said bottom end of said cartridge, said cracking assembly shaped to allow said bone cement monomer to flow past said cracking assembly into said coupling member;
    an ampoule containing the bone cement monomer disposed within said cartridge above said shattering assembly, said ampoule having a surface that faces said cracking assembly;
    a plunger reciprocally mounted to said cartridge adjacent said top end of said cartridge, said plunger dimensioned to, when depressed in said cartridge, press said ampoule against said cracking assembly so that the surface of said ampoule facing said cracking assembly shatters;
    a first pressure-actuated valve attached to said cartridge that is normally closed and that is configured to open when a pressure within the cartridge void space is below an ambient air pressure so as to allow air into the cartridge void space; and
    a second pressure-actuated valve located adjacent the bottom end of said cartridge that is normally closed and that is configured to open when said pressure within the cartridge void space is above the ambient air pressure so as to allow the bone cement monomer to exit said cartridge through said second valve and said coupling member.

2. The apparatus for storing and discharging bone cement monomer of claim 1, wherein:
    said ampoule is formed from glass; and
    said cracking assembly is configured to shatter the surface of said ampoule facing said cracking assembly.

3. The apparatus for storing and discharging bone cement monomer of claim 1, further including a strainer located in said cartridge before said coupling member for straining portions of the ampoule out of the flow of the bone cement monomer through said coupling member.

4. The apparatus for storing and discharging bone cement monomer of claim 3, wherein said strainer consists of a plate disposed in the bottom end of said cartridge, said plate being formed with a plurality of openings.

5. The apparatus for storing and discharging bone cement monomer of claim 1, wherein said cracking assembly consists of a plurality of upwardly extending spikes.

6. The apparatus for storing and discharging bone cement monomer of claim 5, wherein each said spike has a tip and a first said spike has a tip located closer to said ampoule than the tip of a second said spike.

7. The apparatus for storing and discharging bone cement monomer of claim 1, wherein:
    said plunger further includes a grasping assembly for holding said ampoule to said plunger so that said ampoule moves with said plunger; and
    at least one finger that is moveably attached to at least one of said cartridge or said plunger, said finger being moveable relative to said plunger so as to have: an engaged state in which said finger blocks movement of said plunger and said ampoule towards said cracking assembly;
    and a disengaged state in which said finger does not inhibit movement by said plunger that moves said ampoule against said cracking assembly.

8. An apparatus for storing and discharging bone cement monomer, said apparatus including:
    a cartridge having: opposed first and second ends; a void space between the ends; and an outlet opening adjacent the second end;
    an ampoule containing bone cement monomer disposed within the cartridge void space;
    a plunger moveably mounted to said cartridge adjacent the first end of said cartridge, said plunger having a grasping mechanism for holding said ampoule to said plunger so that said ampoule moves with said cartridge, wherein said plunger is moveably mounted to said cartridge to selectively move said ampoule towards and away from the second end of said cartridge;
    a cracking assembly located in said cartridge between said ampoule and the outlet opening, said cracking assembly positioned so that said plunger can move said ampoule against said cracking assembly and having a feature that, when said ampoule is moved against said cracking assembly, opens said ampoule and said cracking assembly being further shaped to define an opening in said cartridge through which monomer is able to flow towards the cartridge outlet opening;
    at least one finger that is moveably attached to at least one of said cartridge or plunger so as to have: an engaged state in which said finger blocks movement of said plunger and said ampoule towards said cracking assembly;

and a disengaged state in which said finger does not inhibit movement by said plunger that moves said ampoule against said cracking assembly;

a first pressure-actuated valve attached to said cartridge that is normally closed and that is configured to open when a pressure within the cartridge void space is below an ambient air pressure so as to allow air into the cartridge void space; and a second pressure-actuated valve located adjacent the second end of said cartridge that is normally closed and that is configured to open when the pressure within the cartridge void space is above said ambient air pressure so as to allow the bone cement monomer to exit said cartridge through said second valve and the cartridge outlet opening.

9. The apparatus for storing and discharging bone cement monomer of claim 8, further including a coupling member adjacent the cartridge outlet opening, said coupling member configured to attach said cartridge to a bone cement mixer so the monomer flows through the outlet opening into the bone cement mixer.

10. The apparatus for storing and discharging bone cement monomer of claim 8, wherein said ampoule is formed from glass.

11. The apparatus for storing and discharging bone cement monomer of Claim 8, wherein said plunger grasping mechanism includes at least one flexible member that presses against said ampoule.

12. The apparatus for storing and discharging bone cement monomer of Claim 8, wherein said cracking assembly feature for opening said ampoule is formed from metal.

13. The apparatus for storing and discharging bone cement monomer of Claim 8, wherein said at least one finger is removably attached to said cartridge or said plunger.

14. The apparatus for storing and discharging bone cement monomer of claim 8, wherein:
said first valve is configured to open when there is a small difference in the pressure between the cartridge void space and the ambient atmospheric pressure; and
said second valve is configured to open when there is a large difference in pressure between the cartridge void space and the ambient atmospheric pressure.

15. An apparatus for storing and discharging bone cement monomer, said apparatus including:
a cartridge having: opposed first and second ends; a void space between said ends; and an outlet opening in the second end;
an ampoule containing bone cement monomer disposed within the cartridge void space;
a cracking assembly located in said cartridge between said ampoule and the outlet opening, said cracking assembly having a feature that, when said ampoule is pressed against said cracking assembly, opens said ampoule and said cracking assembly further defining at least one opening in said cartridge through which monomer is able to flow towards the cartridge outlet opening;

a plunger reciprocally mounted in said cartridge adjacent the first end of said cartridge, said plunger dimensioned to, when depressed towards the cartridge second end, press said ampoule against said cracking assembly, so as to cause said cracking assembly to open said ampoule so as to cause the release of the monomer in the ampoule;

a first pressure-actuated valve attached to said cartridge that is normally closed and that is configured to open when a pressure within the cartridge void space is below an ambient air pressure so as to allow air into the cartridge void space, wherein said first valve opens when there is a small difference in pressure between the pressure in the cartridge void space and the ambient air pressure; and a second pressure-actuated valve located adjacent the second end of said cartridge that is normally closed and that is configured to open when the pressure within the cartridge void space is above said ambient air pressure so as to allow the bone cement monomer to exit said cartridge through said second valve and the cartridge outlet opening, wherein said second valve opens when there is a large difference in pressure between the pressure in the cartridge void space and the ambient air pressure.

16. The apparatus for storing and discharging bone cement monomer of claim 15, wherein said first valve is mounted to said plunger.

17. The apparatus for storing and discharging bone cement monomer of claim 15, further including a coupling member adjacent the cartridge outlet opening, said coupling member configured to attach said cartridge to a bone cement mixer so the monomer flows through the outlet opening into the bone cement mixer.

18. The apparatus for storing and discharging bone cement monomer of claim 15, wherein:
said cracking assembly includes a plate disposed in said cartridge, said plate being formed with holes; and
said cracking assembly feature for opening said ampoule extends upwardly from said plate.

19. The apparatus for storing and discharging bone cement monomer of claim 15, wherein said ampoule is formed from glass.

20. The apparatus for storing and discharging bone cement monomer of claim 15, further including a strainer located in said cartridge between said cracking assembly feature for opening said ampoule and the cartridge outlet opening for straining portions of the ampoule from the flow of the bone cement monomer through the outlet opening.

* * * * *